(12) United States Patent
Yokoi et al.

(10) Patent No.: US 8,053,580 B2
(45) Date of Patent: Nov. 8, 2011

(54) SALTS OF BENZIMIDAZOLE DERIVATIVE WITH AMINES AND PROCESS FOR MANUFACTURING THE SAME

(75) Inventors: Hiroyuki Yokoi, Kamisu (JP); Masanori Mizuno, Kamisu (JP); Toyokazu Haga, Kamisu (JP)

(73) Assignee: Eisal R&D Management Co., Ltd., Tokyo (JP)

( * ) Notice: Subject to any disclaimer, the term of this patent is extended or adjusted under 35 U.S.C. 154(b) by 364 days.

(21) Appl. No.: 12/490,420

(22) Filed: Jun. 24, 2009

(65) Prior Publication Data

US 2009/0264659 A1 Oct. 22, 2009

Related U.S. Application Data

(62) Division of application No. 11/632,931, filed as application No. PCT/JP2005/014400 on Aug. 5, 2005, now Pat. No. 7,829,718.

(30) Foreign Application Priority Data

Aug. 6, 2004 (JP) ................. 2004-230094

(51) Int. Cl.
 *C07D 401/12* (2006.01)
(52) U.S. Cl. ................. 546/273.7
(58) Field of Classification Search ........... 546/273.7
 See application file for complete search history.

(56) References Cited

U.S. PATENT DOCUMENTS

| | | | |
|---|---|---|---|
| 5,045,552 A | 9/1991 | Souda et al. | |
| 5,840,910 A | 11/1998 | Souda et al. | |
| 5,998,445 A | 12/1999 | Souda et al. | |

FOREIGN PATENT DOCUMENTS

| | | |
|---|---|---|
| EP | 0 124 495 A2 | 11/1984 |
| EP | 1 000 943 A1 | 5/2000 |
| EP | 1 270 555 A1 | 1/2003 |
| IN | 192030 | 7/2004 |
| JP | 64-6270 A | 1/1989 |
| JP | 6-74272 B2 | 9/1994 |
| JP | 7-69888 A | 3/1995 |
| JP | 11-71370 A | 3/1999 |
| JP | 2000-143659 A | 5/2000 |
| JP | 2001-039975 A | 2/2001 |
| WO | WO-94/27988 A1 | 12/1994 |
| WO | WO-01/68594 A1 | 9/2001 |
| WO | WO-03/074514 A1 | 9/2003 |
| WO | WO-2004/085424 A1 | 10/2004 |

*Primary Examiner* — Patricia Morris

(74) *Attorney, Agent, or Firm* — Birch, Stewart, Kolasch & Birch, LLP

(57) ABSTRACT

It is an object of the present invention to provide (1) a process for manufacturing alkali metal salts of 2-[{4-(3-methoxypropoxy)-3-methylpyridin-2-yl}methylsulfinyl]-1H-benzimidazole which are useful as gastric acid secretion inhibitors, anti-ulcer agents and other drugs and (2) salts of 2-[{4-(3-methoxypropoxy)-3-methylpyridin-2-yl}methylsulfinyl]-1H-benzimidazole with amines which are intermediates for the production of the alkali metal salts, and a process for manufacturing the same. According to the present invention, disclosed are salts represented by the following formula (I):

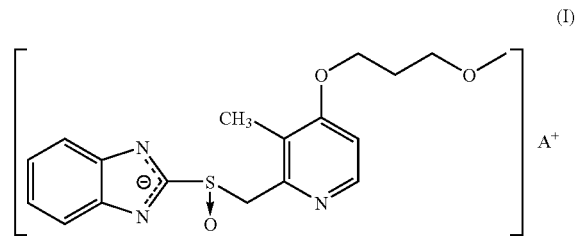

(wherein $A^+$ represents an isopropylammonium ion, sec-butylammonium ion or cyclopentylammonium ion).

1 Claim, 3 Drawing Sheets

SALTS OF BENZIMIDAZOLE DERIVATIVE WITH AMINES AND PROCESS FOR MANUFACTURING THE SAME

This application is a Divisional application which priority is claimed under 35 U.S.C. §120 to U.S. application Ser. No. 11/632,931 filed on Jan. 19, 2007 now U.S. Pat. No. 7,829,718. Application Ser. No. 11/632,931 is the national phase of PCT International Application No. PCT/JP2005/014400 filed on Aug. 5, 2005 and claims priority under 35 U.S.C. §119(a) to Patent Application No. 2004-230094 filed in Japan on Aug. 6, 2004, all of which are hereby expressly incorporated by reference, into the present application.

TECHNICAL FIELD

The present invention relates to (1) a process for manufacturing alkali metal salts of 2-[{4-(3-methoxypropoxy)-3-methylpyridin-2-yl}methylsulfinyl]-1H-benzimidazole which are useful as gastric acid secretion inhibitors, anti-ulcer agents and other drugs and (2) salts of 2-[{4-(3-methoxypropoxy)-3-methylpyridin-2-yl}methylsulfinyl]-1H-benzimidazole with amines which are intermediates for the production of the alkali metal salts, and a process for manufacturing them.

BACKGROUND ART

Alkali metal salts of 2-[{4-(3-methoxypropoxy)-3-methylpyridin-2-yl}methylsulfinyl]-1H-benzimidazole are known to be useful as anti-ulcer agents and the like because they have the effect of inhibiting gastric acid secretion (see for example U.S. Pat. No. 5,045,552).

Although salts of the proton pump inhibitor omeprazole with amines are known (see for example International Patent Publications (pamphlets) WO 03/74514 and WO 94/27988 and European Patent Publication 124495), salts of 2-[{4-(3-methoxypropoxy)-3-methylpyridin-2-yl}methylsulfinyl]-1H-benzimidazole with amines are not known.

The crystallization process of salts of compounds such as omeprazole that act as proton pump inhibitors with amines is also not known to be useful for removing impurities and the like.

Moreover, no method is known of obtaining alkali metal salts of 2-[{4-(3-methoxypropoxy)-3-methylpyridin-2-yl}methylsulfinyl]-1H-benzimidazole from salts of 2-[{4-(3-methoxypropoxy)-3-methylpyridin-2-yl}methylsulfinyl]-1H-benzimidazole with amines.

On the other hand, methods are known of manufacturing a 2-[{4-(3-methoxypropoxy)-3-methylpyridin-2-yl}methylsulfinyl]-1H-benzimidazole sodium salt in which the content of the impurity (2-[{4-(3-methoxypropoxy)-3-methylpyridin-2-yl}methylsulfonyl]-1H-benzimidazole (hereinafter simply referred to as "sulfone") is reduced to between 0.82% and 0.30% (see for example European Patent Publication 1000943).

DISCLOSURE OF THE INVENTION

When m-chloroperbenzoic acid or the like is used as an oxidizing agent in the final step of manufacturing 2-[{4-(3-methoxypropoxy)-3-methylpyridin-2-yl}methylsulfinyl]-1H-benzimidazole, which is useful as an anti-ulcer agent, the sulfone, (2-[{4-(3-methoxypropoxy)-3-methylpyridin-2-yl}methylsulfonyl]-1H-benzimidazole), may occur as an impurity.

Because it is difficult for this sulfone to be separated and purified, there is a demand for a new purification method capable of more efficiently removing the sulfone and providing a better yield of 2-[{4-(3-methoxypropoxy)-3-methylpyridin-2-yl}methylsulfinyl]-1H-benzimidazole.

The inventors of the present invention perfected the present invention as a result of exhaustive research after discovering a purification method for efficiently removing the sulfone which is the issue in the preparation of 2-[{4-(3-methoxypropoxy)-3-methylpyridin-2-yl}methylsulfinyl]-1H-benzimidazole, along with salts of 2-[{4-(3-methoxypropoxy)-3-methylpyridin-2-yl}methylsulfinyl]-1H-benzimidazole with amines that are useful in this purification method.

That is, in the first aspect of the present invention, there is provided:

[1] a salt represented by the following formula (I):

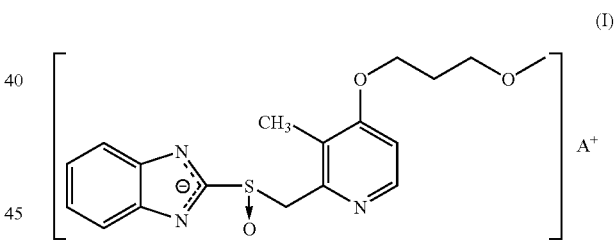

(wherein $A^+$ represents an isopropylammonium ion, sec-butylammonium ion or cyclopentylammonium ion).

Moreover, in another aspect of the present invention, there are provided:

[2] a salt represented by the following formula (II):

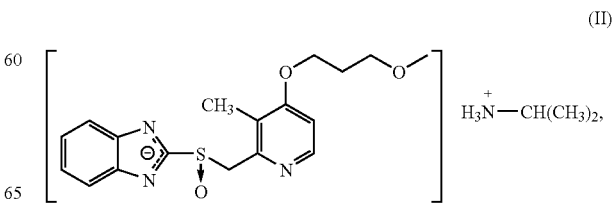

[3] a salt represented by the following formula (III):

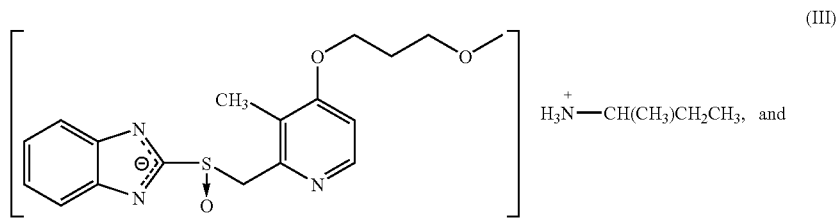

[4] a salt represented by the following formula (IV):

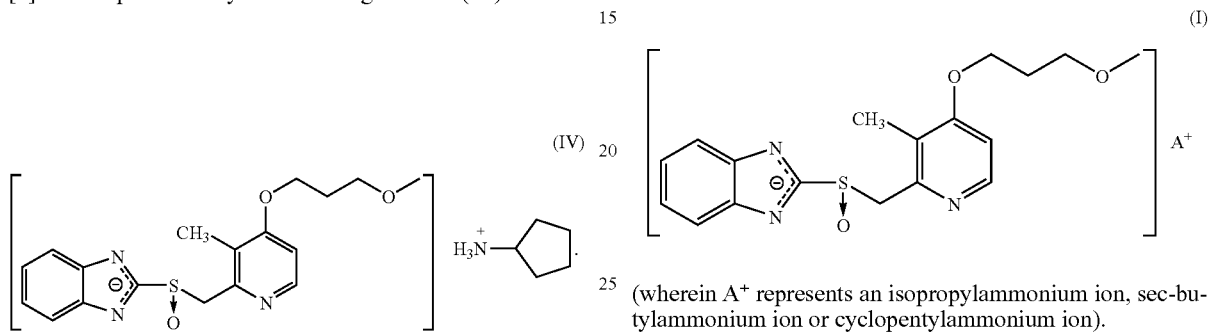

Moreover, in the second aspect of the present invention, there are provided:

[5] a process for manufacturing salt comprising a salt-producing step, wherein the salt-producing step is accomplished in an ester solvent, a nitrile solvent, an ether solvent, an alcohol solvent, a ketone solvent, an aliphatic hydrocarbon solvent, an aromatic hydrocarbon solvent, water or a mixed solvent of the foregoing to produce the salt represented by the following formula (I):

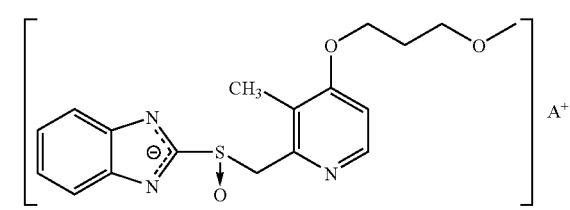

(wherein $A^+$ represents an isopropylammonium ion, sec-butylammonium ion or cyclopentylammonium ion), and

[6] a process for manufacturing a salt comprising a salt-producing step, wherein the salt-producing step is accomplished in ethyl acetate, n-butyl acetate, diethyl carbonate, acetonitrile, t-butylmethyl ether, isopropanol, hexane, tetrahydrofuran, toluene or a mixed solvent of the foregoing to produce the salt represented by the following formula (I):

(I)

(wherein $A^+$ represents an isopropylammonium ion, sec-butylammonium ion or cyclopentylammonium ion).

Moreover, in the third aspect of the present invention, there are provides:

[7] a process for manufacturing a 2-[{4-(3-methoxypropoxy)-3-methylpyridin-2-yl}methylsulfinyl]-1H-benzimidazole alkali metal salt (V), comprising reacting a salt represented by the following formula (I):

(I)

(wherein $A^+$ represents an isopropylammonium ion, sec-butylammonium ion or cyclopentylammonium ion) with a base containing an alkali metal.

[7-1] In a preferred aspect of the process for manufacturing (V) in the present invention, the reaction with the base containing an alkali metal is followed by crystallization, precipitation by salt-producing, or lyophilization in the manufacturing method described in the above [7].

[7-2] In a preferred aspect of the process for manufacturing (V) in the present invention, an acetone complex of 2-[{4-(3-methoxypropoxy)-3-methylpyridin-2-yl}methylsulfinyl]-1H-benzimidazole alkali metal salt (V) is manufactured and then heat-dried in the manufacturing method described in the above [7].

[7-3] In a preferred aspect of the process for manufacturing according to above [7-2], heat-drying is followed by crystallization, precipitation by salt-producing, or lyophilization.

[7-4] In a preferred aspect of the process for manufacturing according to the above [7-2] or [7-3], the heat-drying temperature is from 30° C. to 130° C.

[7-5] In a preferred aspect of the process for manufacturing according to the above [7-2] or [7-3], the heat-drying temperature is from 100° C. to 110° C.

[7-6] In a preferred aspect of the process for manufacturing according to any of the above [7-2] to [7-5], heat-drying is performed under a reduced pressure.

Moreover, in the fourth aspect of the present invention, there are provides:

[8] a gastric acid secretion inhibitor comprising a 2-[{4-(3-methoxypropoxy)-3-methylpyridin-2-yl}methylsulfinyl]-1H-benzimidazole alkali metal salt (V) and 2-[{4-(3-methoxypropoxy)-3-methylpyridin-2-yl}methylsulfonyl]-1H-benzimidazole (VI) in an amount of 0.2% or less,

[8-1] a 2-[{4-(3-methoxypropoxy)-3-methylpyridin-2-yl}methylsulfinyl]-1H-benzimidazole alkali metal salt (V) comprising a 2-[{4-(3-methoxypropoxy)-3-methylpyridin-2-yl}methylsulfonyl]-1H-benzimidazole (VI) content of 0.2% or less (percentage based on combined weight of compounds (V) and (VI),

[9] a therapeutic and/or preventive agent for a disorder caused by gastric acid, comprising a 2-[{4-(3-methoxypropoxy)-3-methylpyridin-2-yl}methylsulfinyl]-1H-benzimidazole alkali metal salt (V) and 2-[{4-(3-methoxypropoxy)-3-methylpyridin-2-yl}methylsulfonyl]-1H-benzimidazole (VI) in an amount of 0.2% or less, and

[10] the therapeutic and/or preventive agent according to the above [9], wherein the disorder caused by gastric acid is gastric ulcer, duodenal ulcer, stomal ulcer, reflux esophagitis, Zollinger-Ellison syndrome, symptomatic reflux esophagitis, endoscopy negative reflux esophagitis, gastroesophageal reflux disease, laryngopharyngeal abnormalities, Barrett's esophagus, NSAID ulcer, gastritis, gastric bleeding, gastrointestinal bleeding, peptic ulcer, bleeding ulcer, stress ulcer, gastric hyperacidity, indigestion, gastric insufficiency, senile ulcer, intractable ulcer, acute gastric mucosal lesions, heartburn, tooth grinding, stomach pain, heavy stomach, temporomandibular arthrosis or gastric erosions.

[11] In a preferred aspect of the therapeutic and/or preventive agent according to the above [9] or [10], the disorder caused by gastric acid is gastric ulcer, duodenal ulcer, stomal ulcer, reflux esophagitis, Zollinger-Ellison syndrome or symptomatic reflux esophagitis.

[12] In a preferred aspect of the therapeutic and/or preventive agent according to any of the above [9] to [11], the disorder caused by gastric acid is reflux esophagitis or symptomatic reflux esophagitis.

[13] In a preferred aspect of the therapeutic and/or preventive agent according to any of the above [9] to [11], the disorder caused by gastric acid is gastric ulcer or duodenal ulcer.

Moreover, in still another aspect of the present invention, there are provides:

[14] an antibacterial or antibacterial adjuvant against gastric *Helicobacter pylori* comprising a 2-[{4-(3-methoxypropoxy)-3-methylpyridin-2-yl}methylsulfinyl]-1H-benzimidazole alkali metal salt (V) and 2-[{4-(3-methoxypropoxy)-3-methylpyridin-2-yl}methylsulfonyl]-1H-benzimidazole (VI) in an amount of 0.2% or less; and

[15] a maintenance therapy agent for reflux esophagitis and/or symptomatic reflux esophagitis comprising a 2-[{4-(3-methoxypropoxy)-3-methylpyridin-2-yl}methylsulfinyl]-1H-benzimidazole alkali metal salt (V) and 2-[{4-(3-methoxypropoxy)-3-methylpyridin-2-yl}methylsulfonyl]-1H-benzimidazole (VI) in an amount of 0.2% or less.

In the term "2-[{4-(3-methoxypropoxy)-3-methylpyridin-2-yl}methylsulfinyl]-1H-benzimidazole alkali metal salt (V) and 2-[{4-(3-methoxypropoxy)-3-methylpyridin-2-yl}methylsulfonyl]-1H-benzimidazole (VI) in an amount of 0.2% or less", the term "2-[{4-(3-methoxypropoxy)-3-methylpyridin-2-yl}methylsulfonyl]-1H-benzimidazole (VI) in an amount of 0.2% or less" means 0.2% or less based on the combined weight of compound (V) and compound (VI).

In the above [8], [8-1], [9], [14] or [15], the content of compound (VI) based on the combined weight of compounds (V) and (VI) is 0.2% or less, preferably about 0.15% or less, more preferably about 0.15% to 0.01%, still more preferably about 0.1% to 0.01%.

Advantageous Effect of the Invention

According to the present invention, the sulfone contained as an impurity can be efficiently removed by using salts of 2-[{4-(3-methoxypropoxy)-3-methylpyridin-2-yl}methylsulfinyl]-1H-benzimidazole with amines when manufacturing 2-[{4-(3-methoxypropoxy)-3-methylpyridin-2-yl}methylsulfinyl]-1H-benzimidazole, which is useful as a drug.

BEST MODE FOR CARRYING OUT THE INVENTION

Figure 1:
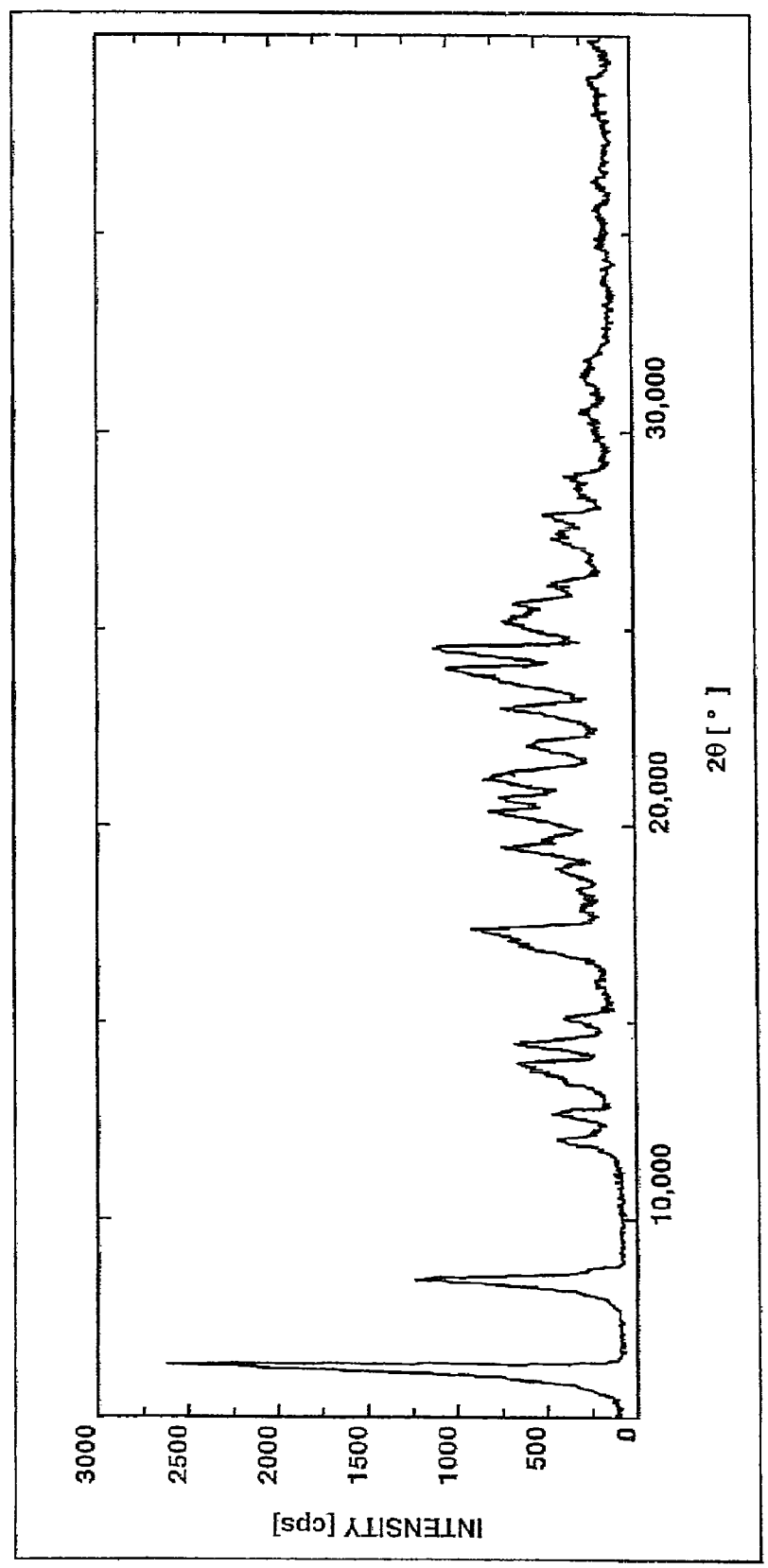
FIG. 1 shows the powder x-ray diffraction pattern of the salt obtained in Example 1X-1 of the present invention.

The following embodiments are illustrative to explain the present invention, and the present invention is not limited to only these embodiments. The present invention can be carried out in various forms so long as the gist of the present invention is not deviated from.

The present invention provides salts for efficiently removing impurities produced during the manufacture of 2-[{4-(3-methoxypropoxy)-3-methylpyridin-2-yl}methylsulfinyl]-1H-benzimidazole, which is useful as a gastric acid secretion inhibitor, anti-ulcer agent or other drug, along with a process for manufacturing such salts.

2-[{4-(3-Methoxypropoxy)-3-methylpyridin-2-yl}methylsulfinyl]-1H-benzimidazole represented by the formula (VII) is the compound represented by the formula (VIIa), the compound represented by the formula (VIIb) or a mixture of compound (VIIa) and (VIIb) in any proportions, and is preferably a 1:1 mixture of compounds (VIIa) and (VIIb):

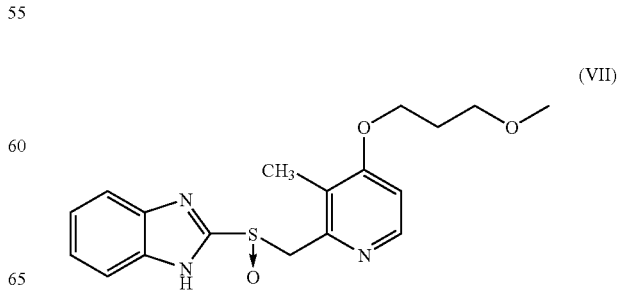

(VII)

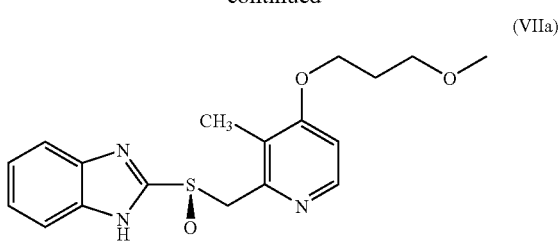

(VIIa)

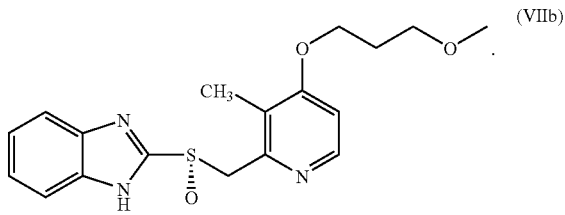

(VIIb)

The salt represented by the formula (I) in the present invention:

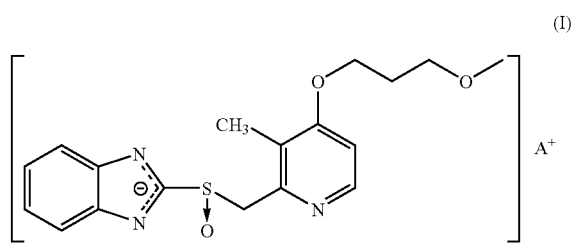

(I)

is a salt of compound (VII) with one amine selected from the group consisting of isopropylamine, sec-butylamine and cyclopentylamine, and is a salt formed by compound (VII) and the aforementioned amine in any proportions. Preferably, it is a salt formed by compound (VII) and the aforementioned amine in proportions of approximately 1:1.

The salt represented by Formula (I) is not particularly limited as long as it is a salt formed by compound (VII) and one amine selected from the group consisting of isopropylamine, sec-butylamine and cyclopentylamine, but example aspects thereof include the salt represented by the following the formula (VIII):

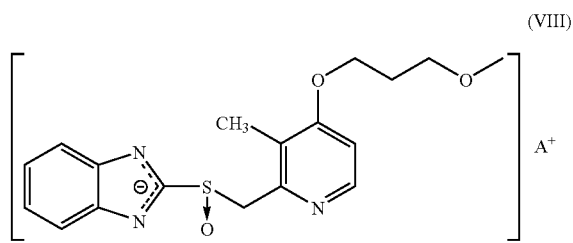

(VIII)

(wherein $A^+$ represents an isopropylammonium ion, sec-butylammonium ion or cyclopentylammonium ion), or the salt represented by the following formula (IX):

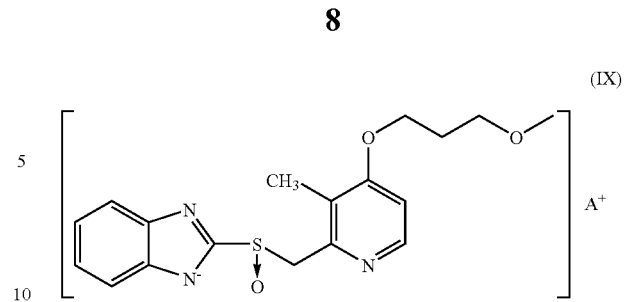

(IX)

(wherein $A^+$ represents an isopropylammonium ion, sec-butylammonium ion or cyclopentylammonium ion)

The term "ester solvent" used in the present invention refers to a $C_{3-7}$ alkyl ester compound, and specific examples of the ester solvent include methyl acetate, ethyl acetate, n-propyl acetate (acetic acid n-propyl ester), s-propyl acetate (acetic acid s-propyl ester), n-butyl acetate (acetic acid n-butyl ester), dimethyl carbonate, diethyl carbonate or the like, with ethyl acetate, n-butyl acetate or the like being preferable examples.

The term "nitrile solvent" used in the present invention refers to a $C_{2-6}$ alkyl nitrile, and a specific example is acetonitrile.

The term "ether solvent" used in the present invention refers to a $diC_{1-6}$ alkyl ether or cyclic ether, and specific examples of the ether solvent include dimethyl ether, t-butyl methyl ether tetrahydrofuran or the like, with t-butyl methyl ether, tetrahydrofuran and the like being preferable examples.

The term "alcohol solvent" used in the present invention refers to a $C_{1-6}$ alkyl alcohol, and specific examples of the alcohol solvent include ethanol, isopropanol, n-propanol or the like, with isopropanol or the like being preferable examples.

The term "ketone solvent" used in the present invention refers to a $diC_{1-6}$ alkyl ketone, and specific examples of the ketone solvent include dimethyl ketone, methyl ethyl ketone or the like.

The term "aliphatic hydrocarbon solvent" used in the present invention refers to a $C_{5-8}$ alkane, and specific examples of the aliphatic hydrocarbon include hexane, heptane or the like, with hexane or the like being preferable example.

The term "aromatic hydrocarbon solvent" used in the present invention refers to a benzene which may have a substitutional group ($C_{1-6}$ alkyl group, $C_{1-6}$ alkoxy group, nitrile group, halogen group or the like), and specific examples of the aromatic hydrocarbon solvent include toluene, xylene, benzene or the like, with toluene or the like being preferable example.

The term "alkali metal salt" used in the present invention is not particularly limited as long as it is a salt with an alkali metal, but specific examples of the alkali metal salt include sodium salts, potassium salts or the like, with sodium salts or the like being preferable example.

The term "base containing an alkali metal" used in the present invention is not particularly limited as long as it is a base containing an alkali metal such as sodium, potassium or the like, but specific examples of the base containing the alkali metal include sodium hydroxide, sodium ethoxide, sodium methoxide, sodium hydride, potassium hydroxide, potassium ethoxide, potassium methoxide, potassium hydride and solutions of the foregoing, as well as ion exchange resins for converting to alkali metal salts, with sodium hydroxide or a sodium hydroxide solution being preferable examples, and sodium hydroxide or a sodium hydroxide aqueous solution, sodium hydroxide methanol solution or sodium hydroxide ethanol solution being more preferable examples.

The term "acetone complex of a 2-[{4-(3-methoxypropoxy)-3-methylpyridin-2-yl}methylsulfinyl]-1H-benzimidazole alkali metal salt" used in the present invention is not particularly limited as long as it is crystals of a 2-[{4-(3-methoxypropoxy)-3-methylpyridin-2-yl}methylsulfinyl]-1H-benzimidazole alkali metal salt containing acetone, but specifically it may be the acetone complex of the 2-[{4-(3-methoxypropoxy)-3-methylpyridin-2-yl}methylsulfinyl]-1H-benzimidazole alkali metal salt described in International Publication Pamphlet WO 04/085424 or European Patent Publication 1000943.

The term "disorder caused by gastric acid" used in the present invention is not particularly limited as long as it is a disorder caused by secretion of gastric acid, but specific examples of the disorder caused by gastric acid include gastric ulcer, duodenal ulcer, stomal ulcer, reflux esophagitis, Zollinger-Ellison syndrome, symptomatic reflux esophagitis, endoscopy negative reflux esophagitis, gastroesophageal reflux disease, laryngopharyngeal abnormalities, Barrett's esophagus, NSAID ulcer, gastritis, gastric bleeding, gastrointestinal bleeding, peptic ulcer, bleeding ulcer, stress ulcer, gastric hyperacidity, indigestion, gastric insufficiency, senile ulcer, intractable ulcer, acute gastric mucosal lesions, heartburn, tooth grinding, stomach pain, heavy stomach, temporbmandibular arthrosis and gastric erosions, with gastric ulcer, duodenal ulcer, stomal ulcer, reflux esophagitis, Zollinger-Ellison syndrome or symptomatic reflux esophagitis being preferred, reflux esophagitis, symptomatic reflux esophagitis, gastric ulcer or duodenal ulcer being more preferable examples, and (1) reflux esophagitis or symptomatic reflux esophagitis or (2) gastric ulcer or duodenal ulcer being most preferable examples.

The present invention also provides an antibacterial agent or antibacterial adjuvant against *Helicobacter pylori* containing the salt represented by the above formula (I) or a solvate thereof. The term "preventive agent" may be an agent that is administered before occurrence of a disorder, or one administered after healing for purposes of maintenance therapy or to prevent recurrence. The aforementioned "antibacterial adjuvant" is an agent that prepares the environment so as to allow the functioning of an antibacterial agent that does not function well under the acidic conditions.

The gastric acid secretion inhibitor and therapeutic and/or preventive agent for the disorders caused by gastric acid of the present invention contains the 2-[{4-(3-methoxypropoxy)-3-methylpyridin-2-yl}methylsulfinyl]-1H-benzimidazole alkali metal salt (V) and 2-[{4-(3-methoxypropoxy)-3-methylpyridin-2-yl}methylsulfonyl]-1H-benzimidazole (VI) in an amount of 0.2% or less, and may be mixed as necessary with known pharmaceutically acceptable carriers (for example, excipients, binders, disintegrators, lubricants, colorants, flavorings, stabilizers, emulsifiers, absorbefacients, surfactants, pH adjusters, preservatives, antioxidants, etc.) and other components commonly used as raw materials in the drug preparations, and prepared by ordinary methods. The preparation may be in a tablet, a powder, a granule, a grain, capsule, a syrup, a suppository or an injection form or the like.

There are no particular limitations on the mode of administration of the gastric acid secretion inhibitor and therapeutic and/or preventive agent for the disorders caused by gastric acid of the present invention, which is preferably administered orally or parenterally. The dosage of the gastric acid secretion inhibitor and therapeutic and/or preventive agent for the disorders caused by gastric acid of the present invention is from 1 to 500 mg/day or preferably from 1 to 200 mg/day or more preferably from 5 to 135 mg/day, depending on symptoms, age and the like.

General Manufacturing Processes

Manufacturing Process A

Process for manufacturing salts of 2-[{4-(3-methoxypropoxy)-3-methylpyridin-2-yl}methylsulfinyl]-1H-benzimidazole with amines The compound (2-[{4-(3-methoxypropoxy)-3-methylpyridin-2-yl}methylsulfinyl]-1H-benzimidazole) (VII) used as the starting material in the manufacturing process according to the present invention can be manufactured by the process described in U.S. Pat. No. 5,045,552 or by the known improvement on this process (for example, Japanese Patent Applications Laid-open Nos. H11-71370 & 2000-143659, International Patent Publication (pamphlet) WO 01/68594, European Patent Publication 1,270,555, etc.). The compound (VII) used as the starting raw material may either include or not include the sulfone, (2-[{4-(3-methoxypropoxy)-3-methylpyridin-2-yl}methylsulfonyl]-1H-benzimidazole) (VI).

An organic solvent and an amine (isopropylamine, sec-butylamine or cyclopentylamine) are added to dissolve 2-[{4-(3-methoxypropoxy)-3-methylpyridin-2-yl}methylsulfinyl]-1H-benzimidazole (with heating if desired). This solution is then stirred at 30 to −40° C. (preferably −20 to −40° C.). The stirring time is not particularly limited but is preferably from 1 hour to 1 day or more preferably overnight (from 10 to 12 hours). Crystals are deposited in a step of cooling and stirring.

Seed crystals (a small amount of crystals of a salt of 2-[{4-(3-methoxypropoxy)-3-methylpyridin-2-yl}methylsulfinyl]-1H-benzimidazole with an amine) may be added or not added during this crystal deposition step. The temperature for adding the seed crystals is not particularly restricted but is preferably 55° C. or less or more preferably from 35° C. to 0° C. A solvent such as hexane, acetic acid n-butyl ester or t-butyl methyl ether can be added as appropriate before crystal deposition or during step of crystal deposition.

Crystals deposited in the mixture can be filtered out to obtain the target salt of 2-[{4-(3-methoxypropoxy)-3-methylpyridin-2-yl}methylsulfinyl]-1H-benzimidazole with the amine.

The resulting crystals can be washed as necessary in the same solvent used for dissolution. The resulting crystals can then be dried as necessary at room temperature or with heating, either at a normal pressure or under a reduced pressure.

There are no particular limitations on the aforementioned organic solvent, but specific examples of the organic solvent include ester solvents, nitrile solvents, ether solvents, alcohol solvents, ketone solvents, aliphatic hydrocarbon solvents, aromatic hydrocarbon solvents, water and mixed solvents of the foregoing, and one or more solvents selected from the group consisting of ethyl acetate, n-butyl acetate, diethyl carbonate, tetrahydrofuran, acetonitrile, t-butyl methyl ether, hexane, isopropanol and toluene is preferred. The amount of the organic solvent used is selected appropriately taking the smallest amount at which compound (VII) is dissolved by heating as the lower limit and the largest amount at which the crystal yield does not decline dramatically as the upper limit, but preferably 3 to 30 times by volume of the weight of compound (VII) (v/w) or more preferably 5 to 20 times by volume of the weight of compound (VII) (v/w) is used.

The amount of amine used is not particularly limited as long as it is at least equivalent to the amount of compound (VII), but it is preferably from 1 to 10 times the molar amount of compound (VII) or more preferably from 5 to 10 times the molar amount of compound (VII) or still more preferably about 7 times the molar amount of compound (VII).

Manufacturing Process B

Synthesis of 2-[{4-(3-methoxypropoxy)-3-methylpyridin-2-yl}methylsulfinyl]-1H-benzimidazole alkali metal salt from salt of 2-[{4-(3-methoxypropoxy)-3-methylpyridin-2-yl}methylsulfinyl]-1H-benzimidazole with amine This step can be accomplished by the ordinary methods of converting amine salts of organic compounds into alkali metal salts thereof. Specifically, a salt of 2-[{4-(3-methoxypropoxy)-3-methylpyridin-2-yl}methylsulfinyl]-1H-benzimidazole with an amine is dissolved in 1 to 3 solvents selected from the group consisting of toluene, methanol, ethanol, water, acetone, ethyl acetate, acetonitrile, t-butyl methyl ether, tetrahydrofuran, hexane and isopropanol, and about 1 equivalent of a base (sodium hydroxide, sodium ethoxide, sodium methoxide, sodium hydride, potassium hydroxide, potassium ethoxide, potassium methoxide, potassium hydride or a solution of the foregoing or the like) is added to the mixture and stirred. The 2-[{4-(3-methoxypropoxy)-3-methylpyridin-2-yl}methylsulfinyl]-1H-benzimidazole alkali metal salt can be obtained by evaporating the solvent from this mixture.

This alkali metal salt can be obtained by crystallization, sedimentation by salt-producing or lyophilization from the mixture or a concentrated residue thereof. This alkali metal salt can also be manufactured by a suitable combination of a step of manufacturing acetone-containing crystals (an acetone complex) of 2-[{4-(3-methoxypropoxy)-3-methylpyridin-2-yl}methylsulfinyl]-1H-benzimidazole and a high-temperature drying step (International Publication Pamphlet WO 04/085424, European Patent Publication 1000943).

The resulting 2-[{4-(3-methoxypropoxy)-3-methylpyridin-2-yl}methylsulfinyl]-1H-benzimidazole alkali metal salt can also be dried at 30° C. to 60° C. under a reduced pressure or at a normal pressure. This drying step can be performed either statically or with shaking, under ventilation if desired.

Manufacturing Process C

Manufacturing step of 2-[{4-(3-methoxypropoxy)-3-methylpyridin-2-yl}methylsulfinyl]-1H-benzimidazole The compound (VII) used as the starting raw material in the manufacturing process according to the present invention can be manufactured by the methods shown below.

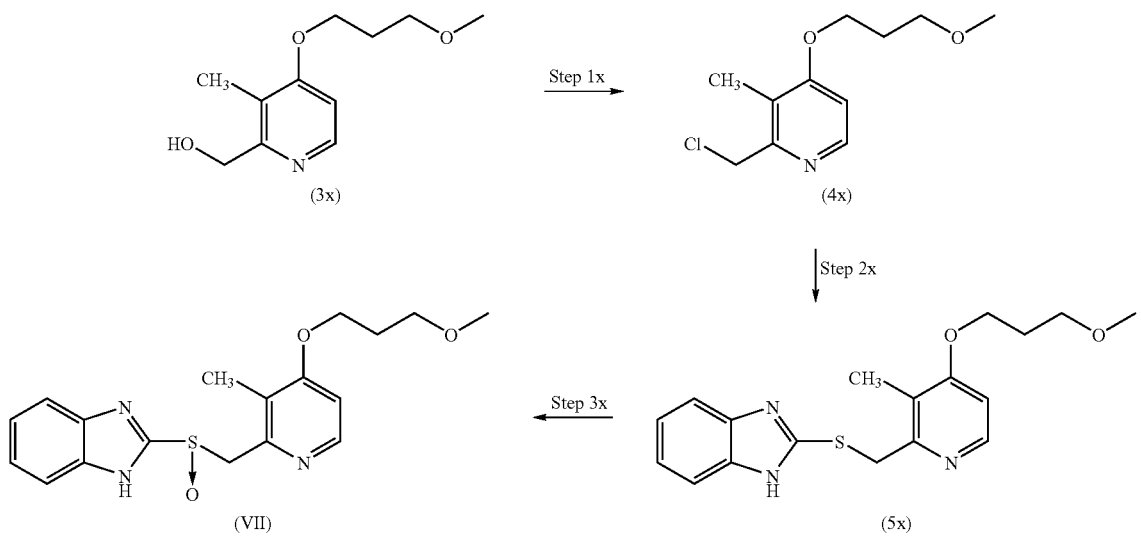

The compound represented by the formula (3x) above (hereinafter simply referred to as "compound (3x)"; the same applies to the compounds represented by the formulae (4x) and (5x)) through compound (5) are all known compounds.

(Step 1x)

This step is a step wherein the crude compound (4x) is manufactured by reacting compound (3x) with a chlorinating agent in an inactive solvent and concentrating the resulting reaction mixture. The inactive solvent used in this step is not particularly limited as long as it can dissolve the raw material compounds somewhat without impeding the reaction. Preferable examples of the inactive solvent used in this step include aromatic hydrocarbons such as benzene, toluene or xylene, organic acid esters such as methyl acetate or ethyl acetate, ethers such as diethyl ether, diisopropyl ether, tetrahydrofuran, dioxane or dimethoxyethane, halogenated hydrocarbons such as methylene chloride, chloroform, carbon tetrachloride or dichloroethane, or the like. It is especially preferable to use toluene, ethyl acetate, dimethoxyethane or dichloromethane.

Examples of the chlorinating agent used in this step include phosphorus trichloride, phosphorus pentachloride, phosphorus oxychloride, thionyl chloride or the like can be used as the chlorinating agent in this step, but preferably one is used such as thionyl chloride that can be evaporated together with the solvent.

The reaction temperature for this step varies depending on the solvents, the raw material compounds and the chlorinating agents used or the like, but is generally from −20° C. to 50° C. or preferably from 0 to 30° C. The reaction time for this step varies depending on the solvents, the raw material compounds, the chlorinating agents, reaction temperature or the like, but is generally from 30 minutes to 6 hours or preferably from 1 to 2 hours.

After completion of the reaction, (1) quenching, (2) concentration and drying of the reaction mixture and (3) purification, etc. are performed as appropriate. To quench the reaction, for example a suitable amount of water or a lower alcohol (particularly ethanol) can be added to the reaction mixture.

After quenching and concentration and drying of the reaction mixture, the reaction mixture can be used as is in Step 2x without any particular purification, and preferably it is used as is after quenching with only slight concentration and drying and purification.

(Step 2x)

This step is a step wherein compound (5x) is manufactured by reacting 2-benzimidazole thiol with compound (4x) obtained in Step 1 in the presence of a base. The inactive solvent used in this step is not particularly limited as long as it can dissolve the raw material compounds somewhat without impeding the reaction, but for example, it is preferable to use alcohols such as methanol, ethanol, propanol, isopropanol, butanol or tert-butanol, aromatic hydrocarbons such as benzene, toluene or xylene or a mixed solvent of the foregoing.

The base used in this step is not particularly limited as long as it dissolves to a certain extent in the solvent. Examples of the base include alkali metal hydrides such as sodium hydroxide or potassium hydroxide, and sodium hydroxide is preferred. The reaction temperature for this step varies depending on the solvent, the raw material compounds and the base used or the like, but is generally from −20° C. to 70° C. or preferably from 20 to 70° C.

The reaction time for this step varies depending on the solvent, the raw material compounds, the base, the reaction temperature or the like, but is generally from 30 minutes to 6 hours, preferably from 1 to 2 hours.

After completion of the reaction, compound (5x) can be separated from the reaction mixture by the standard methods. For example, after completion of the reaction the reaction mixture can be concentrated under a reduced pressure and then extracted with water and an organic solvent not miscible with water (such as dichloromethane, ethyl acetate, methyl acetate, n-butyl acetate or toluene), and the organic layer can then be washed with aqueous sodium hydroxide solution and water and concentrated to manufacture compound (5x). After completion of the reaction the reaction mixture can also be washed with water and used in Step 3x without any concentration or purification.

In particular, a highly pure compound (5x) can be manufactured as a crystal using an organic solvent such as the following:

ethers such as diethyl ether, diisopropyl ether, t-butyl methyl ether, tetrahydrofuran, dioxane or dimethoxyethane (particularly diisopropyl ether or t-butyl methyl ether);

nitriles such as acetonitrile (particularly acetonitrile);

aromatic hydrocarbons such as benzene, toluene or xylene (particularly toluene);

alcohols such as methanol, ethanol, propanol or isopropanol (particularly isopropanol);

ketones such as acetone or methyl ethyl ketone (particularly acetone);

organic acid esters such as methyl acetate, ethyl acetate, dimethyl carbonate or diethyl carbonate (particularly ethyl acetate or diethyl acetate); or a mixed solvent containing at least two of these solvents.

The amount of solvent used during crystallization varies according to the type of solvent, but is from 3 to 40 ml based on 1 g of compound (5).

(Step 3x)

This step is a step wherein compound (1) is manufacturing by reacting compound (5x) with an oxidizing agent in an inactive solvent. The inactive solvent used in this step is not particularly limited as long as it can dissolve the raw material compounds somewhat without impeding the reaction. Preferable examples of the inactive solvent include halogenated hydrocarbons such as chloroform, dichloromethane, carbon tetrachloride or dichloroethane, aromatic hydrocarbons such as benzene, toluene or xylene, alcohols such as methanol, ethanol, propanol, isopropanol, butanol or tert-butanol, or a mixed solvent of the foregoing, with dichloromethane, toluene, methanol, ethanol or a mixed solvent of the foregoing being particularly preferable.

Examples of the oxidizing agent used in this step include hydrogen peroxide, peracetic acid, m-chloroperbenzoic acid, sodium periodate or the like, m-chloroperbenzoic acid being preferably used, in an amount of from 0.3 to 1.1 equivalents based on compound (5×).

The reaction temperature for this step varies depending on the solvent, raw material compounds and the oxidizing agent used or the like, but is generally from −50° C. to 0° C., preferably from −40° C. to −10° C. The reaction time for this step varies depending on the solvent, the raw material compounds, the oxidizing agent, reaction temperature or the like, but is generally from 30 minutes to 6 hours, preferably from 1 to 2 hours.

After completion of the reaction, compound (1) can be separated from the reaction mixture by the standard methods, for example by performing the following operations in sequence:

(Operation 1): a basic aqueous solution (such as an aqueous solution of an alkali metal hydroxide, particularly an aqueous sodium hydroxide solution) is added to the resulting reaction mixture, followed by vigorous stirring or shaking and then standing, and the organic layer is separated to obtain water layer (a);

(Operation 2): an organic solvent (for example, a halogenated hydrocarbon such as chloroform, dichloromethane, carbon tetrachloride or dichloroethane, an organic acid ester such as ethyl acetate, methyl acetate or n-butyl acetate, an aromatic hydrocarbon such as toluene, an alcohol including butanol and mixtures of these) is added to water layer (a), followed by vigorous stirring or shaking and then standing, and the organic layer is separated to obtain water layer (b);

(Operation 3): the same organic solvent is added to water layer (b), which is then vigorously stirring or shaking and then allowed to stand in a state of a pH of 8.0 to 11.0, and separated to obtain organic layer (a) and water layer (c) (an aqueous buffer solution such as an aqueous ammonium acetate solution or acetic acid can be added here as appropriate);

(Operation 4): the same organic solvent is added to water layer (c), followed by vigorous stirring or shaking and then standing, organic layer (b) is separated and combined with organic layer (a), and water or sodium bicarbonate solution is added to the mixture followed by vigorous stirring or shaking and then standing, after which the water layer is removed and the resulting organic layer (c) is concentrated.

In particular, a highly pure compound (I) can be manufactured as the crystals by crystallization using an organic solvent such as the following after concentration:

ethers such as diethyl ether, diisopropyl ether, t-butyl methyl ether, tetrahydrofuran, dioxane or dimethoxyethane (particularly diethyl ether);

nitriles such as acetonitrile (particularly acetonitrile);

aromatic hydrocarbons such as benzene, toluene or xylene (particularly toluene);

alcohols such as methanol, ethanol, propanol, isopropanol or isobutyl alcohol (particularly isopropanol);

ketones such as acetone or methyl ethyl ketone (particularly acetone);

organic acid esters such as methyl acetate, ethyl acetate, n-butyl acetate, dimethyl carbonate or diethyl carbonate (particularly n-butyl acetate); or a mixture of these solvents (particularly a mixture of a nitrile with an organic acid ester).

The water layer (a) obtained by the above Operation 1 or the water layer (b) obtained by the above Operations 1 and 2 can also be used in manufacturing process A without any concentration or purification.

The present invention will be explained in more detail below using examples and reference examples. However, these are only illustrative and the present invention is not in any way limited thereto.

The term "sulfone (VI)" used in the present invention means (2-[{4-(3-methoxypropoxy)-3-methylpyridin-2-yl}methylsulfonyl]-1H-benzimidazole represented by the following formula:

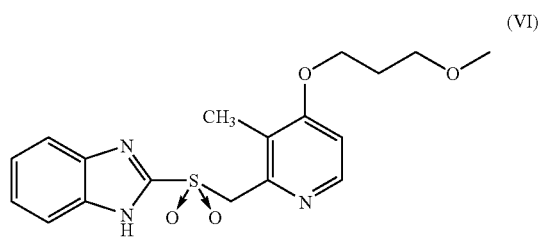

(VI)

The abbreviations used below are defined as follows:
mcpba: meta-chloroperbenzoic acid
TLC: thin-layer chromatography
HPLC: high-performance liquid chromatograph.

EXAMPLES

Synthesis of 2-chloromethyl-4-(3-methoxypropoxy)-3-methylpyridine

Reference Example 1

2-Hydroxymethyl-4-(3-methoxypropoxy)-3-methylpyridine (5.0 g (23.7 mmol)) was dissolved in toluene (40 ml), and thionyl chloride (4.23 g (35.6 mmol)) was added dropwise thereto so that the temperature did not exceed 25° C. Following stirring at room temperature, disappearance of the raw materials was confirmed by TLC, and 2-chloromethyl-4-(3-methoxypropoxy)-3-methylpyridine (6.13 g) was obtained by concentrating under a reduced pressure (yield: 97.3%).

Reference Example 2

2-Hydroxymethyl-4-(3-methoxypropoxy)-3-methylpyridine (5.0 g (23.7 mmol)) was dissolved in ethyl acetate (40 ml), and thionyl chloride (4.23 g (35.6 mmol)) was added dropwise thereto so that the temperature did not exceed 25° C. Following stirring at room temperature, disappearance of the raw materials was confirmed by TLC, and 2-chloromethyl-4-(3-methoxypropoxy)-3-methylpyridine (6.14 g) was obtained by concentrating under a reduced pressure (yield: 97.4%).

Reference Example 3

2-Hydroxymethyl-4-(3-methoxypropoxy)-3-methylpyridine (5.0 g (23.7 mmol)) was dissolved in dimethoxyethane (40 ml), and thionyl chloride (4.23 g (35.6 mmol)) was added dropwise thereto so that the temperature did not exceed 25° C. Following stirring at room temperature, disappearance of the raw materials was confirmed by TLC, and 2-chloromethyl-4-(3-methoxypropoxy)-3-methylpyridine (6.25 g) was obtained by concentrating under a reduced pressure (yield: 99.2%).

Reference Example 4

2-Hydroxymethyl-4-(3-methoxypropoxy)-3-methylpyridine (5.0 g (23.7 mmol)) was dissolved in dichloromethane (40 ml), and thionyl chloride (4.23 g (35.6 mmol)) was added dropwise thereto so that the temperature did not exceed 25° C. Following stirring at room temperature, disappearance of the raw materials was confirmed by TLC, and 2-chloromethyl-4-(3-methoxypropoxy)-3-methylpyridine (6.23 g) was obtained by concentrating under a reduced pressure (yield: 99.0%).

Synthesis of 2-[{4-(3-methoxypropoxy)-3-methylpyridin-2-yl}methylthio]-1H-benzimidazole Reference Example 5-1

2-Chloromethyl-4-(3-methoxypropoxy)-3-methylpyridine (53.2 g (200 mmol)), denatured ethanol (320 ml), 2-benzimidazole thiol (30.2 g (201 mmol)) and sodium hydroxide (26.8 g (670 mmol)) were added together and reacted for about 2 hours at 50° C. After disappearance of the raw materials had been confirmed by TLC, this solution was concentrated under a reduced pressure and ethyl acetate (430 ml) and water (340 ml) were added thereto, followed by stirring and standing, and the water layer was then separated. The organic layer was washed with 10% aqueous sodium hydroxide solution (110 ml) and water (2×110 ml) and concentrated under a reduced pressure to obtain crude 2-[{4-(3-methoxypropoxy)-3-methylpyridin-2-yl}methylthio]-1H-benzimidazole (69.0 g) (HPLC purity 98.7%, yield 101%).

The crude 2-[{4-(3-methoxypropoxy)-3-methylpyridin-2-yl}methylthio]-1H-benzimidazole (5.00 g) was crystallized with ethyl acetate (25 ml) and filtered to obtain 2-[{4-(3-methoxypropoxy)-3-methylpyridin-2-yl}methylthio]-1H-benzimidazole (4.80 g) (HPLC purity 99.2%, yield 96.0%).

Reference Example 5-2

The crude 2-[{4-(3-methoxypropoxy)-3-methylpyridin-2-yl}methylthio]-1H-benzimidazole (5.00 g) obtained in Reference Example 5-1 was crystallized with tert-butyl(methyl) ether (30 m), and filtered to obtain 2-[{4-(3- methoxypropoxy)-3-methylpyridin-2-yl}methylthio]-1H-benzimidazole (4.50 g) (HPLC purity 99.2%), yield 90.0%).

Reference Example 5-3

The crude 2-[{4-(3-methoxypropoxy)-3-methylpyridin-2-yl}methylthio]-1H-benzimidazole (5.00 g) obtained in Reference Example 5-1 was crystallized with diisopropyl ether (200 ml), and filtered to obtain 2-[{4-(3-methoxypropoxy)-3-methylpyridin-2-yl}methylthio]-1H-benzimidazole (4.94 g) (HPLC purity 99.1%, yield 98.8%).

Reference Example 5-4

The crude 2-[{4-(3-methoxypropoxy)-3-methylpyridin-2-yl}methylthio]-1H-benzimidazole (5.00 g) obtained in Reference Example 5-1 was crystallized with toluene (30 ml), and filtered to obtain 2-[{4-(3-methoxypropoxy)-3-methylpyridin-2-yl}methylthio]-1H-benzimidazole (4.56 g) (HPLC purity 99.1%, yield 91.2%).

Reference Example 5-5

The crude 2-[{4-(3-methoxypropoxy)-3-methylpyridin-2-yl}methylthio]-1H-benzimidazole (5.00 g) obtained in Reference Example 5-1 was crystallized with acetonitrile (40 ml), and filtered to obtain 2-[{4-(3-methoxypropoxy)-3-methylpyridin-2-yl}methylthio]-1H-benzimidazole (4.64 g) (HPLC purity 99.1%, yield 92.8%).

Reference Example 5-6

The crude 2-[{4-(3-methoxypropoxy)-3-methylpyridin-2-yl}methylthio]-1H-benzimidazole (5.00 g) obtained in Reference Example 5-1 was crystallized with isopropyl alcohol (20 ml), and filtered to obtain 2-[{4-(3-methoxypropoxy)-3-methylpyridin-2-yl}methylthio]-1H-benzimidazole (4.55 g) (HPLC purity 99.1%, yield 91.0%).

Reference Example 5-7

The crude 2-[{4-(3-methoxypropoxy)-3-methylpyridin-2-yl}methylthio]-1H-benzimidazole (5.00 g) obtained in Reference Example 5-1 was crystallized with acetone (20 ml), and filtered to obtain 2-[{4-(3-methoxypropoxy)-3-methylpyridin-2-yl}methylthio]-1H-benzimidazole (4.80 g) (HPLC purity 99.2%, yield 96.0%).

Reference Example 5-8

The crude 2-[{4-(3-methoxypropoxy)-3-methylpyridin-2-yl}methylthio]-1H-benzimidazole (5.00 g) obtained in Reference Example 5-1 was crystallized with diethyl carbonate (90 ml), and filtered to obtain 2-[{4-(3-methoxypropoxy)-3-methylpyridin-2-yl}methylthio]-1H-benzimidazole (4.85 g) (HPLC purity 99.2%, yield 97.0%).

2-[{4-(3-Methoxypropoxy)-3-methylpyridin-2-yl}methylthio]-1H-benzimidazole-producing step Reference Example 6-1

2-Chloromethyl-4-(3-methoxypropoxy)-3-methylpyridine (26.6 g (100 mmol)), denatured ethanol (160 ml), 2-benzimidazole thiol (15.0 g (100 mmol)) and sodium hydroxide (13.4 g (335 mmol)) were added together and reacted for about 2 hours at 50° C. After disappearance of the raw materials had been confirmed by TLC, this solution was concentrated under a reduced pressure, toluene (30 ml) and water (168 ml) were added thereto. After stirring and still standing the water layer was separated. The organic layer was washed with 10% aqueous sodium hydroxide solution (50 ml) and water (2×50 ml) and concentrated under a reduced pressure to obtain crude 2-[{4-(3-methoxypropoxy)-3-methylpyridin-2-yl}methylthio]-1H-benzimidazole (34.8 g) (HPLC purity 98.7%, yield 101%).

Reference Example 6-2

The crude 2-[{4-(3-methoxypropoxy)-3-methylpyridin-2-yl}methylthio]-1H-benzimidazole (3.00 g) obtained in Reference Example 6-1 was crystallized with ethyl acetate (12 ml), and filtered to obtain 2-[{4-(3-methoxypropoxy)-3-methylpyridin-2-yl}methylthio]-1H-benzimidazole (2.91 g) (HPLC purity 99.3%, yield 97.0%).

Reference Example 6-3

The crude 2-[{4-(3-methoxypropoxy)-3-methylpyridin-2-yl}methylthio]-1H-benzimidazole (3.00 g) obtained in Reference Example 6-1 was crystallized with tert-butyl(methyl) ether (12 ml), and filtered to obtain 2-[{4-(3-methoxypropoxy)-3-methylpyridin-2-yl}methylthio]-1H-benzimidazole (2.79 g) (HPLC purity 99.2%, yield 93.0%).

Reference Example 6-4

The crude 2-[{4-(3-methoxypropoxy)-3-methylpyridin-2-yl}methylthio]-1H-benzimidazole (3.00 g) obtained in Reference Example 6-1 was crystallized with toluene (15 ml), and filtered to obtain 2-[{4-(3-methoxypropoxy)-3-methylpyridin-2-yl}methylthio]-1H-benzimidazole (2.84 g) (HPLC purity 99.1%, yield 94.5%).

Reference Example 6-5

The crude 2-[{4-(3-methoxypropoxy)-3-methylpyridin-2-yl}methylthio]-1H-benzimidazole (3.00 g) obtained in Reference Example 6-1 was crystallized with acetonitrile (21 ml), and filtered to obtain 2-[{4-(3-methoxypropoxy)-3-methylpyridin-2-yl}methylthio]-1H-benzimidazole (2.81 g) (HPLC purity 99.1%, yield 93.5%).

Reference Example 6-6

The crude 2-[{4-(3-methoxypropoxy)-3-methylpyridin-2-yl}methylthio]-1H-benzimidazole (3.00 g) obtained in Reference Example 6-1 was crystallized with diisopropyl alcohol (9 ml), and filtered to obtain 2-[{4-(3-methoxypropoxy)-3-methylpyridin-2-yl}methylthio]-1H-benzimidazole (2.78 g) (HPLC purity 99.4%, yield 92.5%).

Reference Example 6-7

The crude 2-[{4-(3-methoxypropoxy)-3-methylpyridin-2-yl}methylthio]-1H-benzimidazole (3.00 g) obtained in Reference Example 6-1 was crystallized with acetone (9 ml), and filtered to obtain 2-[{4-(3-methoxypropoxy)-3-methylpyridin-2-yl}methylthio]-1H-benzimidazole (2.91 g) (HPLC purity 99.3%, yield 97.0%).

Reference Example 6-8

The crude 2-[{4-(3-methoxypropoxy)-3-methylpyridin-2-yl}methylthio]-1H-benzimidazole (3.00 g) obtained in Reference Example 6-1 was crystallized with diethyl carbonate (45 ml), and filtered to obtain 2-[{4-(3-methoxypropoxy)-3-methylpyridin-2-yl}methylthio]-1H-benzimidazole (2.93 g) (HPLC purity 99.3%, yield 97.5%).

HPLC purity in Reference Examples 5-1 through 6-8 was measured under the following conditions.

HPLC Conditions

| | |
|---|---|
| Column: | Inertsil ODS-2 (GL Sciences) |
| Mobile phase: | Acetonitrile:water:ammonium acetate = 500:500:1 |
| Flow rate: | 0.7 ml/min |
| Column temperature: | 35° C. |
| Detector: | 258 nm |

Synthesis of 2-[{4-(3-methoxypropoxy)-3-methylpyridin-2-yl}methylsulfinyl]-1H-benzimidazole Reference Example 7

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 5.37 g (21.8 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with dichloromethane (14 ml) and acetonitrile (92 ml), and filtered to obtain 2-[{4-(3-methoxypropoxy)-3-methylpyridin-2-yl}methylsulfinyl]-1H-benzimidazole (6.26 g) (HPLC purity 99.7%, yield 23.9%).

Reference Example 8

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 5.37 g (21.8 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with ethyl acetate (66 ml) and filtered to obtain 2-[{4-(3-methoxypropoxy)-3-methylpyridin-2-yl}methylsulfinyl]-1H-benzimidazole (6.15 g) (HPLC purity 99.8%, yield 23.5%).

Reference Example 9

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 7.16 g (29.1 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed twice with water (48 ml), concentrated under a reduced pressure, crystallized with dichloromethane (18 ml) and acetone (120 ml), and filtered to obtain 2-[{4-(3-methoxypropoxy)-3-methylpyridin-2-yl}methylsulfinyl]-1H-benzimidazole (8.56 g) (HPLC purity 99.7%, yield 32.7%).

Reference Example 10

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 7.16 g (29.1 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with isopropyl alcohol (88 ml), and filtered to obtain 2-[{4-(3-methoxypropoxy)-3-methylpyridin-2-yl}methylsulfinyl]-1H-benzimidazole (8.29 g) (HPLC purity 99.7%, yield 31.7%).

Reference Example 11

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 7.16 g (29.1 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with acetonitrile (132 ml), and filtered to obtain 2-[{4-(3-methoxypropoxy)-3-methylpyridin-2-yl}methylsulfinyl]-1H-benzimidazole (8.25 g) (HPLC purity 99.7%, yield 31.5%).

Reference Example 12

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 8.95 g (36.4 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with acetone (165 ml), and filtered to obtain 2-[{4-(3-methoxypropoxy)-3-methylpyridin-2-yl}methylsulfinyl]-1H-benzimidazole (10.8 g) (HPLC purity 99.6%, yield 41.4%).

Reference Example 13

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 8.95 g (36.4 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with toluene (110 ml), and filtered to obtain 2-[{4-(3-methoxypropoxy)-3-methylpyridin-2-yl}methylsulfinyl]-1H-benzimidazole (10.6 g) (HPLC purity 99.6%, yield 40.4%).

Reference Example 14

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 8.95 g (36.4 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with dichloromethane (28 ml) and ethyl acetate (184 ml), and filtered to obtain 2-[{4-(3-methoxypropoxy)-3-methylpyridin-2-yl}methylsulfinyl]-1H-benzimidazole (10.9 g) (HPLC purity 99.7%, yield 41.7%).

Reference Example 15

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 10.7 g (43.7 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with acetone (198 ml), and filtered to obtain 2-[{4-(3-methoxypropoxy)-3-methylpyridin-2-yl}methylsulfinyl]-1H-benzimidazole (12.6 g) (HPLC purity 99.3%, yield 48.3%).

Reference Example 16

2-[{4-(3-Methoxypropoxy)-3-methylpyridin-2-yl}methylthio]-1H-benzimidazole (25.0 g (72.8 mmol)) was dissolved in dichloromethane and cooled. Then, mcpba (70.2% purity; 10.7 g (43.7 mmol)) was added gradually so that the internal temperature did not exceed −15° C. 10% Aqueous sodium hydroxide solution (70.8 ml) was then added, and after stirring and still standing the water layer was separated. The separated water layer was washed with dichloromethane (48 ml) twice. After addition of a 2N-ammonium acetate aqueous solution, the water layer was extracted with dichloromethane (48 ml) twice. The dichloromethane layer was washed with water (48 ml) twice, concentrated under a reduced pressure, crystallized with dichloromethane (27 ml) and ether (220 ml), and filtered to obtain 2-[{4-(3-methoxypropoxy)-3-methylpyridin-2-yl}methylsulfinyl]-1H-benzimidazole (14.5 g) (HPLC purity 99.1%, yield 55.4%).

Reference Example 17

To a mixed solution of 2-hydroxymethyl-4-(3-methoxypropoxy)-3-methylpyridine (12.02 g (56.9 mmol)) and toluene (96.0 ml) was added dropwise thionyl chloride (8.11 g (68.2 mmol)), so that the internal temperature did not exceed 25° C., which was stirred for about 90 minutes at room temperature. Ethanol (24.0 ml) was added to this mixed solution to obtain a 2-chloromethyl-4-(3-methoxypropoxy)-3-methylpyridine solution.

To this 2-chloromethyl-4-(3-methoxypropoxy)-3-methylpyridin solution was added 2-benzimidazole thiol (8.71 g (58.0 mmol)) at room temperature. A 25% aqueous sodium hydroxide solution (40.6 g) was added gradually as the temperature (internal temperature) was gradually raised to 65° C. The reaction mixture was stirred for about an hour and a half at 65° C. (internal temperature). Water (60.0 ml) was added to the reaction mixture at 65° C., after which 25% aqueous sodium hydroxide solution (0.2 g) was added and stirred. This reaction mixture was allowed to stand, and the water layer was separated. The organic layer was washed with water (20.0 ml) twice, and toluene (79.6 ml) and methanol (21.5 ml) were added to the organic layer to obtain a 2-[{4-(3-methoxypropoxy)-3-methylpyridin-2-yl}methylthio]-1H-benzimidazole solution.

This 2-[{4-(3-methoxypropoxy)-3-methylpyridin-2-yl}methylthio]-1H-benzimidazole solution was cooled to 30° C. (external temperature), and a solution of mcpba (70.2% purity; 14.39 g (58.5 mmol)), methanol (12.4 ml) and toluene (10.5 ml) were added over the course of about 1 hour so as not to exceed an internal temperature of −25° C., and then stirred for an hour- and a half. 25% Aqueous sodium hydroxide solution (22.73 g) and water (17.6 ml) were added to the reaction mixture and stirred. This reaction mixture was allowed to stand, and the organic layer was separated to obtain an aqueous alkali solution containing 2-[{4-(3-methoxypropoxy)-3-methylpyridin-2-yl}methylsulfinyl]-1H-benzimidazole.

HPLC purity in Reference Examples 7 through 16 was measured under the following conditions.
HPLC Conditions

| Column: | Nucleosil 5cl8 (Chemco) |
|---|---|
| Mobile phase: | Methanol:Phosphoric acid buffer (pH 7) = 3:2) |
| Flow rate: | 1.0 ml/min |
| Detector: | 290 nm |

The compounds (VII) used as the starting raw materials in Examples 1-1 through 3-1 were compounds containing 1.61%, 1.44%, 0.57%, 0.56% and 0.45% of the sulfone (VI) which can be manufactured by the method described in U.S. Pat. No. 5,045,552 or by the known improvement on this method (for example, Japanese Patent Applications Laid-open Nos. H11-71370 & 2000-143659, International Patent Publication Pamphlet WO 01/68594, European Patent Publication 1,270,555, etc.).

Example 1-1

Synthesis of a salt of 2-[{4-(3-methoxypropoxy)-3-methylpyridin-2-yl}methylsulfinyl]-1H-benzimidazole with isopropylamine To 2-[{4-(3-methoxypropoxy)-3-methylpyridin-2-yl}methylsulfinyl]-1H-benzimidazole (3.00 g, 8.35 mmol, sulfone (VI) content 1.44%) was added acetonitrile (30 ml), which was dissolved at 55° C. (external temperature), and isopropylamine (4.97 ml, 58.4 mmol) was then added. This mixture was cooled at 30° C. (external temperature), hexane (15 ml) and a trace amount of seed crystals (crystals of salt of 2-[{4-(3-methoxypropoxy)-3-methylpyridin-2-yl}methylsulfinyl]-1H-benzimidazole with isopropylamine) were added and stirred for about 2 hours. This mixture was then cooled at −25° C. (external temperature), and stirred overnight. The crystals deposited in the mixture were filtered, washed with acetonitrile (10 ml) cooled at −30° C., and dried under a reduced pressure at room temperature to obtain white crystals of the titled compound (3.30 g; 7.88 mmol, yield 94.5%, sulfone (VI) content 0.02%).

$^1$H-NMR (400 MHz, $CDCL_3$) δ:1.08 (d, J=6.3 Hz, 6H), 2.08 (tt, J=6.1, 6.1 Hz, 2H), 2.20 (s, 3H), 2.84 (brs 3H), 3.11 (sept, J=6.3 Hz, 1H), 3.36 (s, 3H), 3.55 (t, J=6.1 Hz, 2H), 4.11 (t, J=6.1 Hz, 2H), 4.65 (d, J=13.7 Hz, 1H), 4.83 (d, J=13.7 Hz, 1H), 6.75 (d, J=5.9 Hz, 1H), 7.33 (dd, J=3.2, 6.1 Hz, 2H), 7.66 (dd, J=3.2, 6.1 Hz, 2H), 8.31 (d, J=5.9 Hz, 1H).

Note that the sulfone (VI) content was measured by HPLC (high-performance liquid chromatography) under the following conditions.

HPLC Analysis Conditions:

| | |
|---|---|
| Column: | YMC-Pack Pro C18 AS-303 250 mm × 4.6 mm I.D. |
| Mobile phase: | MeOH/$H_2O$/$AcONH_4$ = 550 mL/450 mL/2 g |
| Flow rate: | 1.0 mL/min |
| Detection: | UV 290 nm, column temp. 35° C. |

Example 1-2

Synthesis of a salt of 2-[{4-(3-methoxypropoxy)-3-methylpyridin-2-yl}methylsulfinyl]-1H-benzimidazole with isopropylamine To 2-[{4-(3-methoxypropoxy)-3-methylpyridin-2-yl}methylsulfinyl]-1H-benzimidazole (3.00 g, 8.35 mmol, sulfone (VI) content 0.56%) was added ethyl acetate (45 ml), which was dissolved at 55° C. (external temperature), and isopropylamine (4.97 ml, 58.4 mmol) was then added. This mixture was cooled, and stirred for about 7 hours at room temperature. The crystals deposited in the mixture were filtered, washed with ethyl acetate (20 ml) and dried under a reduced pressure at room temperature to obtain white crystals of the title compound (2.63 g; 6.28 mmol, yield 75.3%, sulfone (VI) content 0.17%).

The resulting salt was confirmed from the NMR data to be the same as that of Example 1-1, and the sulfone content was confirmed under the same conditions as in Example 1-1.

Example 1-3

Synthesis of a salt of 2-[{4-(3-methoxypropoxy)-3-methylpyridin-2-yl}methylsulfinyl]-1H-benzimidazole with isopropylamine Using 2-[{4-(3-methoxypropoxy)-3-methylpyridin-2-yl}methylsulfinyl]-1H-benzimidazole (3.00 g, 8.35 mmol, sulfone (VI) content 0.57%) as the raw material, ethyl acetate (45 ml) was replaced by tetrahydrofuran (15 ml) as the solvent, and ethyl acetate (20 ml) was replaced by tetrahydrofuran (10 ml) for washing the crystals.

White crystals of the title compound (2.64 g; 6.31 mmol, yield 75.6%, sulfone (VI) content 0.02% or less) were then obtained by methods similar to those used in Example 1-2, except for the solvent and the washing solvent.

The resulting salt was confirmed from the NMR data to be the same as that of Example 1-1, and the sulfone content was confirmed under the same conditions as in Example 1-1.

Example 1-4

Synthesis of a salt of 2-[{4-(3-methoxypropoxy)-3-methylpyridin-2-yl}methylsulfinyl]-1H-benzimidazole with isopropylamine Using 2-[{4-(3-methoxypropoxy)-3-methylpyridin-2-yl}methylsulfinyl]-1H-benzimidazole (3.00 g, 8.35 mmol, sulfone (VI) content 1.44%) as the raw material, ethyl acetate (45 ml) was replaced by acetonitrile (30 ml) as the solvent, and overnight stirring after addition of the amine was performed at 0° C. (external temperature).

White crystals of the title compound (2.90 g; 6.93 mmol, yield 83.0%, sulfone (VI) content 0.02% or less) were then obtained by methods similar to those used in Example 1-2, except for the solvent and the stirring conditions.

The resulting salt was confirmed from the NMR data to be the same as that of Example 1-1, and the sulfone content was confirmed under the same conditions as in Example 1-1.

Example 1-5

Synthesis of a salt of 2-[{4-(3-methoxypropoxy)-3-methylpyridin-2-yl}methylsulfinyl]-1H-benzimidazole with isopropylamine Using 2-[{4-(3-methoxypropoxy)-3-methylpyridin-2-yl}methylsulfinyl]-1H-benzimidazole (3.00 g, 8.35 mmol, sulfone (VI) content 1.44%) as the raw material, t-butyl methyl ether (9 ml) was used in place of hexane (15 ml), and overnight stirring after addition of the amine was performed at 0° C. (external temperature).

White crystals of the title compound (2.89 g; 6.91 mmol, yield 82.7%, sulfone (VI) content 0.02% or less) was then obtained by methods similar to those used in Example 1-1, except for the solvent and the stirring conditions The resulting salt was confirmed from the NMR data to be the same as that of Example 1-1, and the sulfone (VI) content was confirmed under the same conditions as in Example 1-1.

Example 1-6

Synthesis of a salt of 2-[{4-(3-methoxypropoxy)-3-methylpyridin-2-yl}methylsulfinyl]-1H-benzimidazole with isopropylamine Using 2-[{4-(3-methoxypropoxy)-3-methylpyridin-2-yl}methylsulfinyl]-1H-benzimidazole (3.00 g, 8.35 mmol, sulfone (VI) content 1.44%) as the raw material, overnight stirring after addition of the amine was performed at 0° C. (external temperature), and the same methods were used as in Example 1-1, except for the stirring conditions, to obtain white crystals of the title compound (3.17 g; 7.57 mmol, yield 90.6%, sulfone (VI) content 0.02% or less).

Example 1-7

Synthesis of a salt of 2-[{4-(3-methoxypropoxy)-3-methylpyridin-2-yl}methylsulfinyl]-1H-benzimidazole with isopropylamine Using 2-[{4-(3-methoxypropoxy)-3-methylpyridin-2-yl}methylsulfinyl]-1H-benzimidazole (3.01 g, 8.37 mmol, sulfone (VI) content 1.44%) as the raw material, the amount of isopropylamine was changed from (4.97 ml, 58.4 mmol) to (2.13 ml, 25.0 mmol).

The amount of hexane was also changed from 15 ml to 9 ml. Overnight stirring after addition of the amine was performed at 0° C. (external temperature), and the same methods were used as in Example 1-1, except for the amounts of the solvent and the amine, to obtain white crystals of the title compound (3.16 g; 7.55 mmol, yield 90.2%, sulfone (VI) content 0.03% or less).

The resulting salt was confirmed from the NMR data to be the same as that of Example 1-1, and the sulfone content was confirmed under the same conditions as in Example 1-1.

Example 1-8

Synthesis of a salt of 2-[{4-(3-methoxypropoxy)-3-methylpyridin-2-yl}methylsulfinyl]-1H-benzimidazole with isopropylamine 2-[{4-(3-Methoxypropoxy)-3-methylpyridin-2-yl}methylsulfinyl]-1H-benzimidazole (3.00 g, 8.35 mmol, sulfone (VI) content 1.44%) was dissolved in acetonitrile (28.1 ml) and isopropylamine (5.0 ml) at 30° C. Then, acetic acid n-butyl ester (23.0 ml) and a trace amount of seed crystals (crystals of salt of 2-[{4-(3-methoxypropoxy)-3-methylpyridin-2-yl}methylsulfinyl]-1H-benzimidazole with isopropylamine) were added, stirred for 1 hour, cooled to −25° C. and then stirred overnight. The deposited crystals were filtered, washed with acetonitrile (5 ml) chilled at −25° C. (external temperature), and dried under a reduced pressure at room temperature to obtain white crystals of the title compound (3.46 g; yield 93.7%, sulfone (VI) content 0.02% or less). The sulfone content was confirmed under the same conditions as in Example 1-1.

$^1$H-NMR (400 MHz, CDCl$_3$) δ: 1.08 (d, J=6.3 Hz, 6H), 2.07 (tt, J=6.1, 6.1 Hz, 2H), 2.18 (s, 3H), 3.11 (sept, J=6.3 Hz, 1H), 3.35 (s, 3H), 3.54 (t, J=6.1 Hz, 2H), 4.09 (t, J=6.1 Hz, 2H), 4.66 (d, J=13.7 Hz, 1H), 4.82 (d, J=13.7 Hz, 1H), 6.73 (d, J=5.6 Hz, 1H), 7.30-7.34 (m, 2H), 7.62-7.67 (m, 2H), 8.30 (d, J=5.6 Hz, 1H).

Example 2-1

Synthesis of a salt of 2-[{4-(3-methoxypropoxy)-3-methylpyridin-2-yl}methylsulfinyl]-1H-benzimidazole with cyclopentylamine To 2-[{4-(3-methoxypropoxy)-3-methylpyridin-2-yl}methylsulfinyl]-1H-benzimidazole (3.00 g, 8.35 mmol, sulfone (VI) content 0.57%) was added toluene (60 ml), which was dissolved at 55° C., and cyclopentylamine (5.76 ml, 58.4 mmol) was then added. This mixture was cooled at −10° C. (external temperature), and stirred overnight.

The crystals deposited in the mixture were filtered, washed with toluene (10 ml) chilled at −30° C., and dried under a reduced pressure at room temperature to obtain white crystals of the title compound (2.97 g; 6.68 mmol, yield 80.0%, sulfone (VI) content 0.06%). The sulfone content was confirmed under the same conditions as in Example 1-1.

$^1$H-NMR (400 MHz, CDCl$_3$) δ: 1.23-1.33 (m, 2H), 1.51-1.58 (m, 2H), 1.66-1.75 (m, 2H), 1.80-1.87 (m, 2H), 2.06 (tt, J=6.1, 6.1 Hz, 2H), 2.17 (s, 3H), 3.30-3.38 (m, 1H), 3.35 (s, 3H), 3.49 (brs 3H), 3.53 (t, J=6.1 Hz, 2H), 4.08 (t, J=6.1 Hz, 2H), 4.70 (d, J=13.7 Hz, 1H), 4.81 (d, J=13.7 Hz, 1H), 6.72 (d, J=5.6 Hz, 1H), 7.31 (dd, J=3.2, 6.1 Hz, 2H), 7.63 (dd, J=3.2, 6.1 Hz, 2H), 8.29 (d, J=5.6 Hz, 1H).

Example 2-2

Synthesis of a salt of 2-[{4-(3-methoxypropoxy)-3-methylpyridin-2-yl}methylsulfinyl]-1H-benzimidazole with cyclopentylamine Using 2-[{4-(3-methoxypropoxy)-3-methylpyridin-2-yl}methylsulfinyl]-1H-benzimidazole (3.01 g, 8.37 mmol, sulfone (VI) content 0.57%) as the raw material, toluene (60 ml) was replaced by ethyl acetate (45 ml) as the solvent, and overnight stirring after addition of the amine was performed at −40° C. (external temperature).

The same methods were used as in Example 2-1, except for the solvent and the stirring conditions, to obtain white crystals of the title compound (3.21 g; 7.22 mmol, yield 86.4%, sulfone (VI) content 0.26%).

The resulting salt was confirmed from the NMR data to be the same as that of Example 2-1, and the sulfone content was confirmed under the same conditions as in Example 1-1.

Example 2-3

Synthesis of a salt of 2-[{4-(3-methoxypropoxy)-3-methylpyridin-2-yl}methylsulfinyl]-1H-benzimidazole with cyclopentylamine Using 2-[{4-(3-methoxypropoxy)-3-methylpyridin-2-yl}methylsulfinyl]-1H-benzimidazole (3.00 g, 8.35 mmol, sulfone (VI) content 0.57%) as the raw material, toluene (60 ml) was replaced by isopropanol (21 ml) as the solvent, and overnight stirring after addition of the amine was performed at −40° C. (external temperature).

The same methods were used as in Example 2-1, except for the solvent and the stirring conditions, to obtain white crystals of the title compound (3.30 g (7.42 mmol, yield 88.9%, sulfone (VI) content 0.26%).

The resulting salt was confirmed from the NMR data to be the same as that of Example 2-1, and the sulfone content was confirmed under the same conditions as in Example 1-1.

Example 2-4

Synthesis of a salt of 2-[{4-(3-methoxypropoxy)-3-methylpyridin-2-yl}methylsulfinyl]-1H-benzimidazole with cyclopentylamine 2-[{4-(3-methoxypropoxy)-3-methylpyridin-2-yl}methylsulfinyl]-1H-benzimidazole (3.00 g, 8.35 mmol, sulfone (VI) content 0.45%) as the raw material was dissolved in acetonitrile (28.1 ml) and cyclopentylamine (5.7 ml). After addition of acetic acid n-butyl ester (23.0 ml), this mixture was cooled to 10° C. and a trace amount of seed crystals (crystals of salt of 2-[{4-(3-methoxypropoxy)-3-methylpyridin-2-yl}methylsulfinyl]-1H-benzimidazole with cyclopentylamine) were added followed by stirring for 1 hour, cooling to −25° C., and overnight stirring was performed. The deposited crystals were filtered, washed with acetonitrile (5 ml) chilled at −25° C. (external temperature), and dried under a reduced pressure at room temperature to obtain white crystals of the title compound (3.35 g; yield 90.3%, sulfone (VI) content 0.06%).

The resulting salt was confirmed from the NMR data to be the same as that of Example 2-1, and the sulfone content was confirmed under the same conditions as in Example 1-1.

Example 3-1

Synthesis of a salt of 2-[{4-(3-methoxypropoxy)-3-methylpyridin-2-yl}methylsulfinyl]-1H-benzimidazole with sec-butylamine To 2-[{4-(3-methoxypropoxy)-3-methylpyridin-2-yl}methylsulfinyl]-1H-benzimidazole (3.00 g, 8.35 mmol, sulfone (VI) content 0.57%) was added ethyl acetate (45 ml), which was dissolved at 55° C., and sec-butylamine (5.90 ml, 58.4 mmol) was then added. This mixture was cooled at −40° C. (external temperature), and stirred overnight.

The crystals deposited in the mixture were filtered, washed with ethyl acetate (10 ml) chilled at −30° C., and dried under a reduced pressure at room temperature to obtain white crystals of the title compound (3.14 g; 7.26 mmol, yield 86.9%, sulfone (VI) content 0.02% or less). The sulfone content was confirmed under the same conditions as in Example 1-1.

$^1$H-NMR (400 MHz, CDCl$_3$) δ: 0.91 (d, J=7.4 Hz, 3H), 1.06 (d, J=6.3 Hz, 3H), 1.31-1.39 (m, 2H), 2.07 (tt, J=6.1, 6.1 Hz, 2H), 2.19 (s, 3H), 2.80 (brs 3H), 2.77-2.84 (m, 1H), 3.36 (s, 3H), 3.55 (t, J=6.1 Hz, 2H), 4.10 (t, J=6.1 Hz, 2H), 4.66 (d, J=13.7 Hz, 1H), 4.82 (d, J=13.7 Hz, 1H), 6.74 (d, J=5.6 Hz, 1H), 7.33 (dd, J=3.2, 6.1 Hz, 2H), 7.66 (dd, J=3.2, 6.1 Hz, 2H), 8.31 (d, J=5.6 Hz, 1H).

Example 3-2

Synthesis of a salt of 2-[{4-(3-methoxypropoxy)-3-methylpyridin-2-yl}methylsulfinyl]-1H-benzimidazole with sec-butylamine 2-[{4-(3-Methoxypropoxy)-3-methylpyridin-2-yl}methylsulfinyl]-1H-benzimidazole (3.00 g, 8.35 mmol, sulfone (VI) content 0.45%) was dissolved in acetonitrile (51.0 ml) and sec-butylamine (5.93 ml). Then, this mixture was cooled to 15° C. and a trace amount of seed crystals (crystals of salt of 2-[{4-(3-methoxypropoxy)-3-methylpyridin-2-yl}methylsulfinyl]-1H-benzimidazole with sec-butylamine) were added followed by stirring for 1 hour, cooling to −25° C., and overnight stirring was performed. The deposited crystals were filtered, washed (external temperature) with acetonitrile (5 ml) chilled at −25° C., and dried under a reduced pressure at room temperature to obtain white crystals of the title compound (3.15 g; yield 87.1%, sulfone (VI) content 0.02% or less).

The resulting salt was confirmed from the NMR data to be the same as that of Example 3-1, and the sulfone content was confirmed under the same conditions as in Example 1-1.

Example 3-3

Synthesis of a salt of 2-[{4-(3-methoxypropoxy)-3-methylpyridin-2-yl}methylsulfinyl]-1H-benzimidazole with sec-butylamine 2-[{4-(3-Methoxypropoxy)-3-methylpyridin-2-yl}methylsulfinyl]-1H-benzimidazole (3.00 g, 8.35 mmol, sulfone (VI) content 1.61%) was dissolved in acetonitrile (28.1 ml) and sec-butylamine (5.9 ml). Then, diethyl carbonate (23.0 ml) was added, followed by cooling to 15° C., and a trace amount of seed crystals (crystals of salt of 2-[{4-(3-methoxypropoxy)-3-methylpyridin-2-yl}methylsulfinyl]-1H-benzimidazole with sec-butylamine) were added followed by stirring for 1 hour, cooling to −25° C., and overnight stirring was performed. The deposited crystals were filtered, washed with acetonitrile (5 ml) chilled at −25° C. (external temperature), and dried under a reduced pressure at room temperature to obtain white crystals of the title compound (3.23 g; yield 89.4%, sulfone (VI) content 0.02% or less).

The resulting salt was confirmed from the NMR data to be the same as that obtained in Example 3-1, and the sulfone content was confirmed under the same conditions as in Example 1-1.

An aqueous sodium hydroxide solution (extract obtained with aqueous sodium hydroxide solution after reaction) of compound (VII) obtained in the above Reference Examples 7-17 or by methods similar to those of Japanese Patent Application Laid-open H11-71.370 (Example 1) was used for the alkali solution of 2-[{4-(3-methoxypropoxy)-3-methylpyridin-2-yl}methylsulfinyl]-1H-benzimidazole which is the starting material in the following Examples 1X-1, 2X-1 and 3X-1.

Example 1X-1

Synthesis of a salt of 2-[{4-(3-methoxypropoxy)-3-methylpyridin-2-yl}methylsulfinyl]-1H-benzimidazole with isopropylamine To an alkali solution (41.77 g (sulfone (VI) content 1.75%)) containing 2-[{4-(3-methoxypropoxy)-3-methylpyridin-2-yl}methylsulfinyl]-1H-benzimidazole (7.37 g) were added water (64.4 ml), toluene (69.4 ml) and 1-butanol (3.7 ml), which was stirred. Then, acetic acid (1.74 g) was added to adjust a pH to 9.0. This mixture solution was separated into a toluene layer and a water layer, and the water layer was further extracted with toluene (54.0 ml), and combined with the previously extracted toluene layer. The combined toluene layer was washed with water (15.4 ml), and concentrated under a reduced pressure after addition of isopropylamine (5.7 ml). To the resulting residue were added acetonitrile (58.0 ml) and isopropylamine (1.9 ml), which was then concentrated again under a reduced pressure. To the concentrated residue were added acetonitrile (62.3 ml) and isopropylamine (10.2 ml), which was stirred at 30° C. Acetic acid n-butyl ester (54.6 ml) and a trace amount of seed crystals (salt of 2-[{4-(3-methoxypropoxy)-3-methylpyridin-2-yl}methylsulfinyl]-1H-benzimidazole with isopropylamine) were added, and the mixture was then cooled to −25° C. (external temperature) and stirred overnight. The deposit was filtered, washed with acetonitrile (15 ml) chilled at −25° C. (external temperature), and dried under a reduced pressure for about 6 hours at room temperature to obtain white crystals of the title compound (7.94 g; yield 92.5%, sulfone (VI) content 0.02% or less). The sulfone content was confirmed under the same conditions as in Example 1-1.

¹H-NMR (400 MHz, CDCl₃) δ: 1.07 (d, J=6.1 Hz, 6H), 2.08 (tt, J=6.1, 6.1 Hz, 2H), 2.20 (s, 3H), 3.11 (sept, J=6.1 Hz, 1H), 3.36 (s, 3H), 3.55 (t, J=6.1 Hz, 2H), 4.11 (t, J=6.1 Hz, 2H), 4.63 (d, J=13.7 Hz, 1H), 4.83 (d, J=13.7 Hz, 1H), 6.75 (d, J=5.6 Hz, 1H), 7.34 (dd, J=3.2, 6.2 Hz, 2H), 7.67 (dd, J=3.2, 6.2 Hz, 2H), 8.32 (d, J=5.6 Hz, 1H).

Example 1X-2

Synthesis of an acetone complex of 2-[{4-(3-methoxypropoxy)-3-methylpyridin-2-yl}methylsulfinyl]-1H-benzimidazole sodium salt To a salt (2.51 g; 60 mmol, sulfone (VI) content 0.02% or less) of 2-[{4-(3-methoxypropoxy)-3-methylpyridin-2-yl}methylsulfinyl]-1H-benzimidazole with isopropylamine were added ethanol (26.1 ml) and ethyl acetate (26.1 ml), which was dissolved at room temperature. To this solution was added 5 mol/L aqueous sodium hydroxide solution (1.11 ml), which was then concentrated under a reduced pressure. To the residue were added ethyl acetate (50.4 ml) and acetone (2.5 ml), which was concentrated again under a reduced pressure. To the resulting solids were added ethyl acetate (18.0 ml) and acetone (12.0 ml). To this mixture solution was added a trace amount of seed crystals (acetone complex of 2-[{4-(3-methoxypropoxy)-3-methylpyridin-2-yl}methylsulfinyl]-1H-benzimidazole sodium salt), which was stirred overnight at room temperature. The deposit was filtered, washed with acetone (7 ml), and dried under a reduced pressure at room temperature to obtain white crystals of the title compound (2.35 g; 5.3 mmol, yield 89.2%).

Example 1X-3

Synthesis of 2-[{4-(3-methoxypropoxy)-3-methylpyridin-2-yl}methylsulfinyl]-1H-benzimidazole sodium salt 2-[{4-(3-Methoxypropoxy)-3-methylpyridin-2-yl}methylsulfinyl]-1H-benzimidazole sodium salt (2.07 g; sulfone (VI) content 0.02% or less) was obtained by the methods similar to those of WO2004-085424, Example 6 using an acetone complex (2.35 g) of 2-[{4-(3-methoxypropoxy)-3-methylpyridin-2-yl}methylsulfinyl]-1H-benzimidazole sodium salt. The sulfone content was confirmed under the same conditions as in Example 1-1.

¹H-NMR (400 MHz, DMSO-d₆) δ: 1.97 (tt, J=6.1, 6.1 Hz, 2H), 2.17 (s, 3H), 3.24 (s, 3H), 3.48 (t, J=6.1 Hz, 2H), 4.09 (t, J=6.1 Hz, 2H), 4.39 (d, J=12.9 Hz, 1H), 4.74 (d, J=12.9 Hz, 1H), 6.85 (dd, J=3.2, 6.1 Hz, 2H), 6.92 (d, J=5.6 Hz, 1H), 7.43 (dd, J=3.2, 6.1 Hz, 2H), 8.27 (d, J=5.6 Hz, 1H).

Example 1X-4

Synthesis of 2-[{4-(3-methoxypropoxy)-3-methylpyridin-2-yl}methylsulfinyl]-1H-benzimidazole sodium salt A salt (2.00 g; 4.8 mmol, sulfone (VI) content 0.02% or less) of 2-[{4-(3-methoxypropoxy)-3-methylpyridin-2-yl}methylsulfinyl]-1H-benzimidazole with isopropylamine, water (5.0 ml) and 5 mol/L aqueous sodium hydroxide solution (0.89 ml) were added together and dissolved by stirring, and then washed with water (1.0 ml) and lyophilized. This was then dried under a reduced pressure for about 21 hours at 50° C. to obtain a white solid of the title compound (1.79 g; 4.7 mmol, yield 98.0%, sulfone (VI) content 0.02% or less). The sulfone content was confirmed under the same conditions as in Example 1-1.

¹H-NMR (400 MHz, DMSO-d₆) δ: 1.97 (tt, J=6.1, 6.1 Hz, 2H), 2.17 (s, 3H), 3.24 (s, 3H), 3.48 (t, J=6.1 Hz, 2H), 4.08 (t, J=6.1 Hz, 2H), 4.39 (d, J=12.7 Hz, 1H), 4.77 (d, J=12.7 Hz, 1H), 6.86 (dd, J=3.2, 6.1 Hz, 2H), 6.91 (d, J=5.6 Hz, 1H), 7.44 (dd, J=3.2, 6.1 Hz, 2H), 8.26 (d, J=5.6 Hz, 1H).

Example 2X-1

Synthesis of salt of 2-[{4-(3-methoxypropoxy)-3-methylpyridin-2-yl}methylsulfinyl]-1H-benzimidazole with cyclopentylamine To an alkali solution (41.66 g (sulfone (VI) content 1.66%)) containing 2-[{4-(3-methoxypropoxy)-3-methylpyridin-2-yl}methylsulfinyl]-1H-benzimidazole (7.38 g) were added water (64.4 ml), toluene (69.4 ml) and 1-butanol (3.7 ml), which was stirred, then acetic acid (1.98 g) and 5 mol/L aqueous sodium hydroxide solution (0.36 g) were added to adjusted a pH to 9.0. This mixture solution was separated into a toluene layer and a water layer, and the water layer was further extracted with toluene (54.0 ml), and the resulting was combined with the previously extracted toluene layer. This combined toluene layer was washed with water (25.9 ml), and concentrated under a reduced pressure after addition of cyclopentylamine (5.9 ml). To the resulting residue were added acetonitrile (58.0 ml) and cyclopentylamine (2.0 ml), which was then further concentrated under a reduced pressure. To the concentrated residue were added acetonitrile (62.3 ml), cyclopentylamine (11.8 ml) and acetic acid n-butyl ester (54.6 ml), which was stirred at 2° C. A trace amount of seed crystals (salt of 2-[{4-(3-methoxypropoxy)-3-methylpyridin-2-yl}methylsulfinyl]-1H-benzimidazole with cyclopentylamine) was added, and after crystal deposition had been confirmed this was stirred for 60 minutes at 30° C. (external temperature) and cooled to −25° C. (external temperature). The deposit was filtered, washed with acetonitrile (10 ml) chilled at −25° C. (external temperature), and dried under a reduced pressure for about 3 hours at room temperature to obtain white crystals of the title compound (8.23 g; yield 90.2%, sulfone (VI) content 0.10%)). The sulfone content was confirmed under the same conditions as in Example 1-1.

¹H-NMR (400 MHz, CDCl₃) δ: 1.24-1.32 (m, 2H), 1.53-1.59 (m, 2H), 1.67-1.73 (m, 2H), 1.79-1.87 (m, 2H), 2.07 (tt, J=6.1, 6.1 Hz, 2H), 2.18 (s, 3H), 3.20 (brs, 3H), 3.30-3.38 (m, 1H), 3.35 (s, 3H), 3.54 (t, J=6.1 Hz, 2H), 4.09 (t, J=6.1 Hz, 2H), 4.66 (d, J=13.7 Hz, 1H), 4.82 (d, J=13.7 Hz, 1H), 6.73 (d, J=5.6 Hz, 1H), 7.32 (dd, J=3.2, 6.1 Hz, 2H), 7.64 (dd, J=3.2, 6.1 Hz, 2H), 8.30 (d, J=5.6 Hz, 1H).

Example 2X-2

Synthesis of a acetone complex of 2-[{4-(3-methoxypropoxy)-3-methylpyridin-2-yl}methylsulfinyl]-1H-benzimidazole sodium salt To a salt (2.51 g (5.6 mmol, sulfone (VI) content 0.10%)) of 2-[{4-(3-methoxypropoxy)-3-methylpyridin-2-yl}methylsulfinyl]-1H-benzimidazole with cyclopentylamine were added ethanol (25.1 ml) and ethyl acetate (25.1 ml), which was dissolved at room temperature. To this solution was added 5 mol/L aqueous sodium hydroxide solution (1.11 ml), which was then concentrated under a reduced pressure. To the resulting residue were added ethyl acetate (50.2 ml) and acetone (2.5 ml), which was further concentrated under a reduced pressure. Ethyl acetate (18.0 ml) and acetone (12.0 ml) were added to dissolve the resulting dry solid. To this mixture solution was added a trace amount of seed crystals (a acetone complex of 2-[{4-(3-methoxypropoxy)-3-methylpyridin-2-yl}methylsulfinyl]-1H-benzimidazole sodium salt), which was stirred overnight at room temperature. The deposit was filtered, washed with acetone (7 ml), and dried under a reduced pressure at room temperature to obtain white crystals of the title compound (2.32 g; 5.3 mmol, yield 93.7%)).

Example 2X-3

Synthesis of 2-[{4-(3-methoxypropoxy)-3-methylpyridin-2-yl}methylsulfinyl]-1H-benzimidazole sodium salt 2-[{4-(3-Methoxypropoxy)-3-methylpyridin-2-yl}methylsulfinyl]-1H-benzimidazole sodium salt (2.04 g (sulfone (VI) content 0.08%)) was obtained by the methods similar to those of WO 2004-085424, Example 6 using an acetone complex (2.32 g) of a 2-[{4-(3-methoxypropoxy)-3-methylpyridin-2-yl}methylsulfinyl]-1H-benzimidazole sodium salt.

The resulting salt was confirmed from the NMR data to be the same as that of Example 1X-3, and the sulfone content was confirmed under the same conditions as in Example 1-1.

Example 2X-4

Synthesis of 2-[{4-(3-methoxypropoxy)-3-methylpyridin-2-yl}methylsulfinyl]-1H-benzimidazole sodium salt To a salt (2.00 g; 4.5 mmol, sulfone (VI) content 0.10%)) of 2-[{4-(3-methoxypropoxy)-3-methylpyridin-2-yl}methylsulfinyl]-1H-benzimidazole with cyclopentylamine were added water (5.0 ml) and a 5 mol/L aqueous sodium hydroxide solution, which was dissolved by stirring, washed with water (1.0 ml) and lyophilized. This was then dried under a reduced pressure for about 21 hours at 50° C. to obtain a white solid of the title compound (1.81 g; 4.7 mmol, yield 105.2%, sulfone (VI) content 0.11%)).

The resulting salt was confirmed from the NMR data to be the same as that of Example 1X-4, and the sulfone content was confirmed under the same conditions as in Example 1-1.

Example 3X-1

Synthesis of a salt of 2-[{4-(3-methoxypropoxy)-3-methylpyridin-2-yl}methylsulfinyl]-1H-benzimidazole with sec-butylamine To an alkali solution (41.66 g (sulfone (VI) content 1.66%)) containing 2-[{4-(3-methoxypropoxy)-3-methylpyridin-2-yl}methylsulfinyl]-1H-benzimidazole (7.38 g) were added water (64.4 ml), toluene (69.4 ml) and 1-butanol (3.7 ml), which was stirred, acetic acid (1.90 g) was then added to adjust a pH to 9.0. This mixture solution was separated into a toluene layer and a water layer, and the water layer was further extracted with toluene (54.0 ml) and the resulting was combined with the previously extracted toluene layer. This combined toluene layer was washed with water (25.9 ml), and concentrated under a reduced pressure after addition of sec-butylamine (6.0 ml). To the resulting residue were added acetonitrile (58.0 ml) and sec-butylamine (2.0 ml), which was concentrated again under a reduced pressure. To the concentrated residue were added acetonitrile (62.3 ml), sec-butylamine (12.3 ml) and acetic acid n-butyl ester (54.6 ml), which was stirred at 12° C. A trace amount of seed crystals (salt of 2-[{4-(3-methoxypropoxy)-3-methylpyridin-2-yl}methylsulfinyl]-1H-benzimidazole with sec-butylamine) was added, and after cooling to −15° C. (external temperature) and confirmation of crystal deposition, this was stirred for 20 minutes at 20° C. (external temperature) and cooled to −25° C. (external temperature). The deposit was filtered, washed with chilled acetonitrile (10 ml) at −25° C. (external temperature), and dried under a reduced pressure for about 3.5 hour at room temperature to obtain white crystals of the title compound (8.10 g; yield 91.3%, sulfone (VI) content 0.02% or less). The sulfone content was confirmed under the same conditions as in Example 1-1.

$^{1}$H-NMR (400 MHz, CDCl$_3$) δ: 0.91 (t, J=7.4 Hz, 3H), 1.06 (d, J=6.3 Hz, 3H), 1.31-1.39 (m, 2H), 2.07 (tt, J=6.1, 6.1 Hz, 2H), 2.18 (s, 3H), 2.76-2.84 (m, 1H), 3.13 (brs, 3H), 3.35 (s, 3H), 3.54 (t, J=6.1 Hz, 2H), 4.09 (t, J=6.1 Hz, 2H), 4.66 (d, J=13.7 Hz, 1H), 4.82 (d, J=13.7 Hz, 1H), 6.73 (d, J=5.6 Hz, 1H), 7.32 (dd, J=3.2, 6.1 Hz, 2H), 7.64 (dd, J=3.2, 6.1 Hz, 2H), 8.30 (d, J=5.6 Hz, 1H).

Example 3X-2

Synthesis of acetone complex of 2-[{4-(3-methoxypropoxy)-3-methylpyridin-2-yl}methylsulfinyl]-1H-benzimidazole sodium salt To a salt (2.61 g (6.0 mmol, sulfone (VI) content 0.02% or less) of 2-[{4-(3-methoxypropoxy)-3-methylpyridin-2-yl}methylsulfinyl]-1H-benzimidazole with sec-butylamine were added ethanol (26.1 ml) and ethyl acetate (26.1 ml), which was dissolved at room-temperature. To this solution was added 5 mol/L aqueous sodium hydroxide solution (1.14 ml), which was then concentrated under a reduced pressure. To the resulting residue were added ethyl acetate (52.2 ml) and acetone (2.6 ml), which was then concentrated again under a reduced pressure. Ethyl acetate (18.0 ml) and acetone (12.0 ml) were added to dissolve the resulting dry solid. To this mixed solution was added a trace amount of seed crystals (acetone complex of 2-[{4-(3-methoxypropoxy)-3-methylpyridin-2-yl}methylsulfinyl]-1H-benzimidazole sodium salt), which was stirred overnight at room temperature. The deposit was filtered, washed with acetone (6 ml), and dried under a reduced pressure at room temperature to obtain white crystals of the title compound (2.36 g; 5.4 mmol, yield 88.9%).

Example 3X-3

Synthesis of 2-[{4-(3-methoxypropoxy)-3-methylpyridin-2-yl}methylsulfinyl]-1H-benzimidazole sodium salt 2-[{4-(3-Methoxypropoxy)-3-methylpyridin-2-yl}methylsulfinyl]-1H-benzimidazole sodium salt (2.08 g; sulfone (VI) content 0.02% or less) was obtained by the methods similar to those of WO 2004-085424, Example 6 using an acetone complex (2.36 g) of a 2-[{4-(3-methoxypropoxy)-3-methylpyridin-2-yl}methylsulfinyl]-1H-benzimidazole sodium salt.

The resulting salt was confirmed from the NMR data to be the same as that of Example 1X-3, and the sulfone content was confirmed under the same conditions as in Example 1-1.

Example 3X-4

Synthesis of 2-[{4-(3-methoxypropoxy)-3-methylpyridin-2-yl}methylsulfinyl]-1H-benzimidazole sodium salt To a salt (2.00 g; 4.6 mmol, sulfone (VI) content 0.02%) of 2-[{4-(3-methoxypropoxy)-3-methylpyridin-2-yl}methylsulfinyl]-1H-benzimidazole with sec-butylamine were added water (5.0 ml) and a 5 mol/L aqueous sodium hydroxide solution (0.87 ml), which was dissolved by stirring, washed with water (1.0 ml) and lyophilized. This was then dried under a reduced pressure for about 21 hours at 50° C. to obtain a white solid of the title compound (1.75 g; 4.6 mmol, yield 99.3%, sulfone (VI) content 0.02% or less).

The resulting salt was confirmed from the NMR data to be the same as that of Example 1X-4, and the sulfone content was confirmed under the same conditions as in Example 1-1.

Measurement of Powder X-Ray Diffraction Pattern

Powder x-ray diffraction measurements of the salts obtained in the Examples were performed under the following measurement conditions in accordance with the powder x-ray diffraction measurement methods described in the general testing methods of the Japanese Pharmacopoeia.

(Equipment)
Rigaku X-ray DTA System: RINT-2000 (Rigaku KK)
(Operating Methods)
Samples were pulverized in an agate mortar, sampled on glass plates, and measured under the following conditions.

| X-ray used: | CuKα |
| --- | --- |
| Lamp voltage: | 40 kV |
| Lamp current: | 20 mA |
| Divergence slit: | 1 deg |
| Receiving slit: | 0.15 mm |
| Scattering slit: | 1 deg |
| Scanning speed: | 2°/min |
| Scanning step: | 0.02° |
| Measurement range (2θ): | 5 to 40° |

Figure 2:
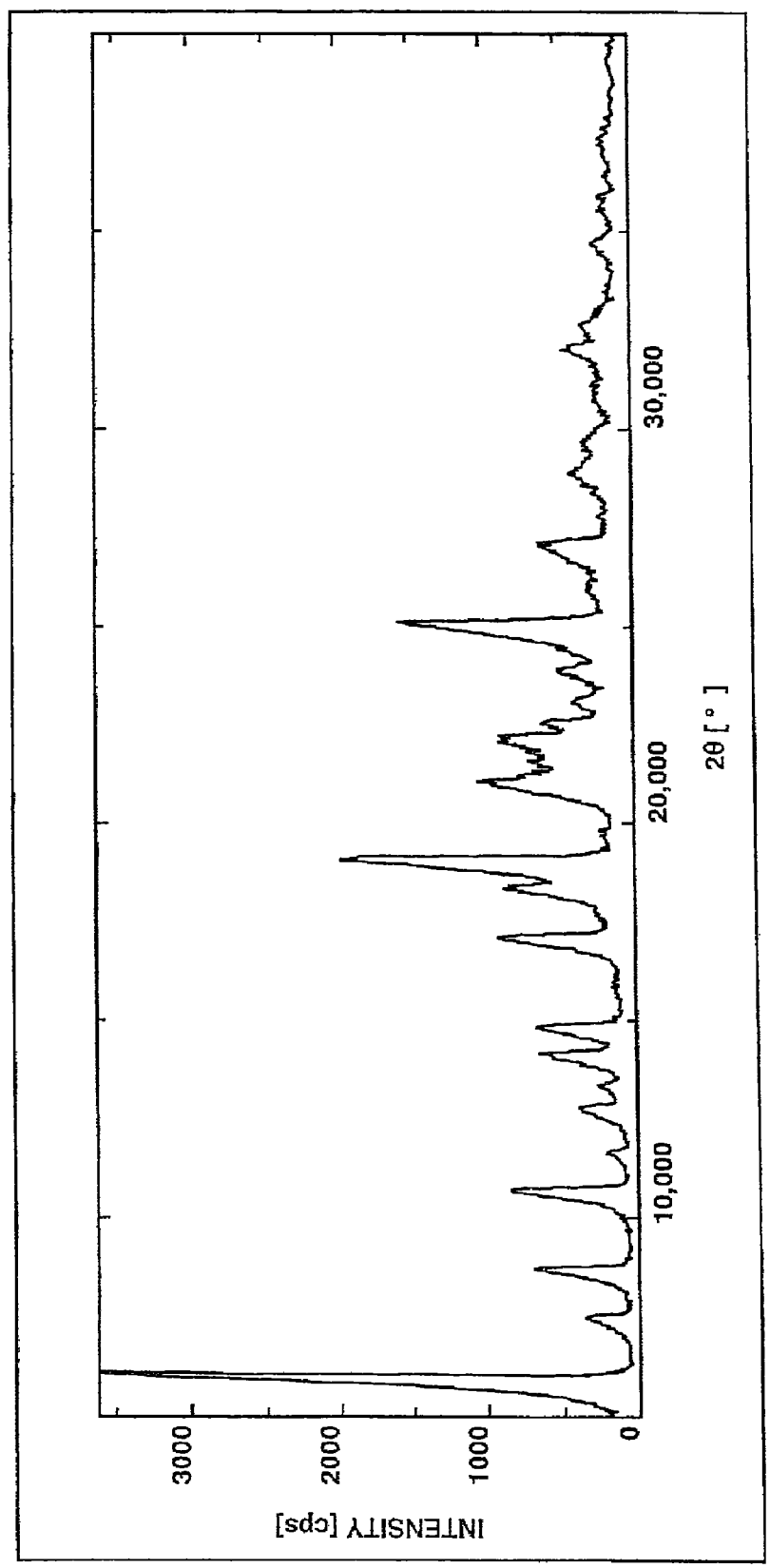
FIG. 2 shows the powder x-ray diffraction pattern of the salt obtained in Example 2X-1 of the present invention.
Figure 3:
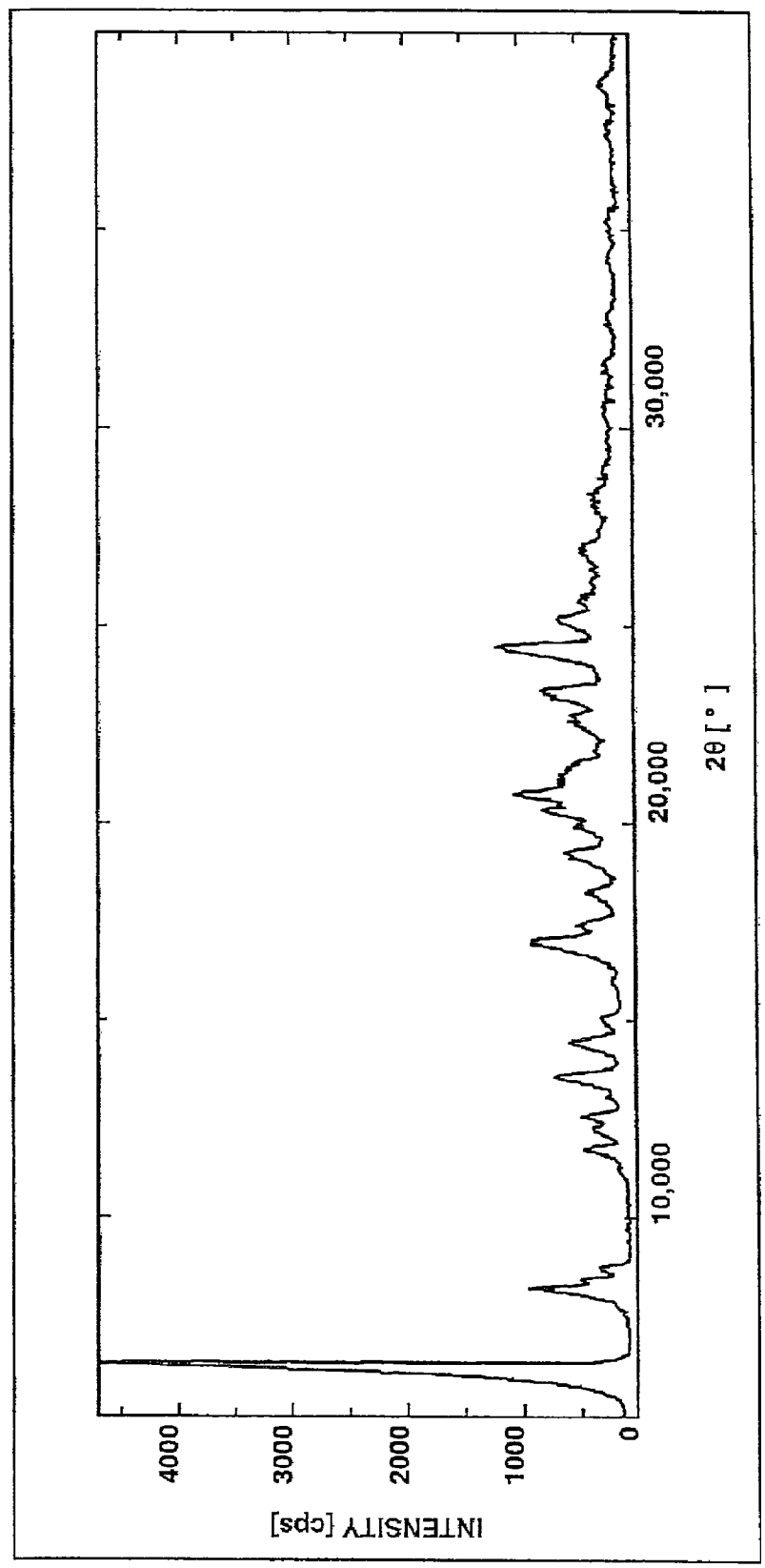
FIG. 3 shows the powder x-ray diffraction pattern of the salt obtained in Example 3X-1 of the present invention.

FIG. 1 shows the powder x-ray diffraction pattern of the salt obtained in Example 1X-1, FIG. 2 shows the powder x-ray diffraction pattern of the salt obtained in Example 2X-1, and FIG. 3 shows the powder x-ray diffraction pattern of the salt obtained in Example 3X-1. As can be seen from the powder x-ray diffraction pattern results in FIGS. 1-3, x-ray diffraction peaks are present in FIGS. 1-3, demonstrating that the salts of 2-[{4-(3-methoxypropoxy)-3-methylpyridin-2-yl}methylsulfinyl]-1H-benzimidazole with isopropylamine, cyclopentylamine and sec-butylamine of the examples were synthesized not in an amorphous state but as salts in a crystalline state.

INDUSTRIAL APPLICABILITY

According to the present invention, the sulfone of 2-[{4-(3-methoxypropoxy)-3-methylpyridin-2-yl}methylsulfinyl]-1H-benzimidazole contained as an impurity can be efficiently removed by using salts of 2-[{4-(3-methoxypropoxy)-3-methylpyridin-2-yl}methylsulfinyl]-1H-benzimidazole with amines when manufacturing 2-[{4-(3-methoxypropoxy)-3-methylpyridin-2-yl}methylsulfinyl]-1H-benzimidazole, which is useful as a drug.

The invention claimed is:
1. A process for manufacturing a 2-[{4-(3-methoxypropoxy)-3-methylpyridin-2-yl}methylsulfinyl]-1H-benzimidazole alkali metal salt (V), comprising reacting a salt represented by the following formula (I):

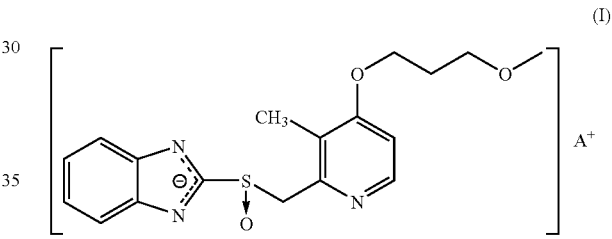

(I)

(wherein $A^+$ represents an isopropylammonium ion, sec-butylammonium ion or cyclopentylammonium ion) with a base containing an alkali metal.

* * * * *